(12) United States Patent
Yang et al.

(10) Patent No.: US 11,434,519 B2
(45) Date of Patent: *Sep. 6, 2022

(54) METHODS AND COMPOSITIONS FOR DIRECT CHEMICAL LYSIS

(71) Applicant: BECTON DICKINSON AND COMPANY, Franklin Lakes, NJ (US)

(72) Inventors: Feng Yang, Cockeysville, MD (US); Sha-Sha Wang, Wellesley, MA (US); Laurence Michael Vaughan, Cockeysville, MD (US); Michael Porter, Baltimore, MD (US); Elaine Rose, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 284 days.

This patent is subject to a terminal disclaimer.

(21) Appl. No.: 16/399,305

(22) Filed: Apr. 30, 2019

(65) Prior Publication Data

US 2019/0256893 A1   Aug. 22, 2019

Related U.S. Application Data

(60) Continuation of application No. 15/067,428, filed on Mar. 11, 2016, now Pat. No. 10,323,267, which is a division of application No. 12/874,602, filed on Sep. 2, 2010, now Pat. No. 10,190,152.

(60) Provisional application No. 61/239,553, filed on Sep. 3, 2009.

(51) Int. Cl.
| | |
|---|---|
| *C12Q 1/68* | (2018.01) |
| *C12N 1/06* | (2006.01) |
| *C12Q 1/70* | (2006.01) |
| *C12Q 1/6806* | (2018.01) |
| *G01N 33/569* | (2006.01) |

(52) U.S. Cl.
CPC ............ *C12Q 1/6806* (2013.01); *C12N 1/06* (2013.01); *C12Q 1/708* (2013.01); *G01N 33/56983* (2013.01); *G01N 2333/025* (2013.01)

(58) Field of Classification Search
CPC .................................. C12N 1/06; C12Q 1/6806
See application file for complete search history.

(56) References Cited

U.S. PATENT DOCUMENTS

| | | |
|---|---|---|
| 3,689,633 A | 9/1972 | Matsushima et al. |
| 4,061,537 A | 12/1977 | Seiler et al. |
| 4,333,847 A | 6/1982 | Iran et al. |
| 4,997,932 A | 3/1991 | Reardon et al. |
| 5,136,025 A | 8/1992 | Scheuermann et al. |
| 5,137,710 A | 8/1992 | Smalley et al. |
| 5,231,015 A | 7/1993 | Cummins et al. |
| 5,248,506 A | 9/1993 | Holme et al. |
| 5,256,571 A | 10/1993 | Hurley et al. |
| 5,376,527 A | 12/1994 | Robson et al. |
| 5,538,871 A | 7/1996 | Nuovo et al. |
| 5,545,555 A | 8/1996 | Racioppi et al. |
| 5,620,869 A | 4/1997 | Woodard et al. |
| 5,700,836 A | 12/1997 | Sheiness et al. |
| 5,766,852 A | 6/1998 | Down et al. |
| 5,837,452 A | 11/1998 | Clark et al. |
| 5,958,300 A | 9/1999 | Chan |
| 10,190,152 B2 * | 1/2019 | Yang ................. G01N 33/56983 |
| 10,323,267 B2 * | 6/2019 | Yang .................... C12Q 1/6806 |
| 2003/0170664 A1 | 9/2003 | Mori et al. |
| 2004/0023207 A1 | 2/2004 | Polansky |
| 2004/0038213 A1 * | 2/2004 | Kwon .................. C12Q 1/6806 435/270 |
| 2004/0101947 A1 | 5/2004 | Engel et al. |

(Continued)

FOREIGN PATENT DOCUMENTS

| | | |
|---|---|---|
| CN | 1243955 | 2/2000 |
| EP | 0511430 | 11/1992 |

(Continued)

OTHER PUBLICATIONS

Baillargeon, J., Piper, J. and Leach, C.T., 2000. Epidemiology of human herpesvirus 6 (HHV-6) infection in pregnant and nonpregnant women. Journal of clinical virology, 16(3), pp. 149-157. (Year: 2000).*

Cuschieri, K.S., Seagar, A.L., Moore, C., Gilkison, G., Kornegay, J. and Cubie, H.A., 2003. Development of an automated extraction procedure for detection of human papillomavirus DNA in liquid based cytology samples. Journal of virological methods, 107(1), pp. 107-113. (Year: 2003).*

Duval et al. Optimized manual and automated recovery of amplifiable DNA from tissues preserved in buffered formalin and alcohol-based fixative. Forensic Sci Int Genet. Feb. 2010; 4(2):80-8. Epub Jul. 8, 2009. (Year: 2009).*

(Continued)

*Primary Examiner* — Teresa E Strzelecka
*Assistant Examiner* — Olayinka A Oyeyemi
(74) *Attorney, Agent, or Firm* — Sheppard, Mullin, Richter & Hampton LLP

(57) ABSTRACT

A direct chemical lysis composition includes an assay compatible buffer composition and an assay compatible surfactant. When combined with a specimen storage composition, such compositions prevent undesired modifications to nucleic acid and proteins lysed from cells in the biological sample. Assays of samples from such compositions do not require expensive and time-consuming steps such as centrifugation and prolonged high temperature processing. The direct chemical lysis composition of the present invention permits direct nucleic acid extraction from the cells in the biological sample without the need to decant off the transport media or otherwise exchange the transport media with assay compatible buffers. There is no need to combine the sample with proteinase K or another enzyme to extract nucleic acids from the cells. A method for lysing cells to obtain target nucleic acid for assay and a kit for combining the direct chemical lysis composition with a sample are also contemplated.

29 Claims, 5 Drawing Sheets

(56) References Cited

U.S. PATENT DOCUMENTS

| | | |
|---|---|---|
| 2005/0032105 A1 | 2/2005 | Bair et al. |
| 2005/0033205 A1 | 2/2005 | Komkin et al. |
| 2005/0164260 A1 | 7/2005 | Chen |
| 2006/0105372 A1 | 5/2006 | Bair et al. |
| 2006/0115844 A1* | 6/2006 | Finkelstein .......... C12Q 1/6806 435/270 |
| 2007/0015185 A1 | 1/2007 | Basehore et al. |
| 2009/0123910 A1 | 5/2009 | Malick et al. |
| 2009/0312285 A1* | 12/2009 | Fischer ................ C12Q 1/6806 514/75 |
| 2010/0063268 A1 | 3/2010 | Kanehara et al. |
| 2011/0065906 A1 | 3/2011 | Liu et al. |
| 2011/0223606 A1 | 9/2011 | McMaster et al. |

FOREIGN PATENT DOCUMENTS

| | | |
|---|---|---|
| EP | 0559208 | 9/1993 |
| EP | 1085098 | 3/2001 |
| EP | 1506995 A1 | 3/2006 |
| JP | 07-250674 | 10/1995 |
| JP | H09505479 A | 6/1997 |
| JP | H11332562 A | 12/1999 |
| JP | 2002541456 A | 12/2002 |
| JP | 2007117084 A | 5/2007 |
| JP | 2007516729 A | 6/2007 |
| JP | 2008043332 A | 2/2008 |
| WO | 94/26867 | 11/1994 |
| WO | 97/11196 A2 | 3/1997 |
| WO | 98/16261 A1 | 4/1998 |
| WO | 99/29890 | 6/1999 |
| WO | 99/31273 | 6/1999 |
| WO | 200057906 A1 | 10/2000 |
| WO | 03/023062 | 3/2003 |
| WO | 03097816 A1 | 11/2003 |
| WO | 2005121373 | 12/2005 |
| WO | 2006023471 A2 | 3/2006 |
| WO | WO 2006923471 A2 | 3/2006 |
| WO | 2006110591 A2 | 10/2006 |
| WO | 2006028616 | 3/2008 |
| WO | 2006053629 | 5/2008 |
| WO | 2009144182 | 12/2009 |
| WO | 20110288887 A2 | 3/2011 |

OTHER PUBLICATIONS

Hoelzle, L.E., Adelt, D., Hoelzle, K., Heinritzi, K. and Wittenbrink, M.M., 2003. Development of a diagnostic PCR assay based on novel DNA sequences for the detection of Mycoplasma suis (Eperythrozoon suis) in porcine blood. Veterinary microbiology, 93(3), pp. 185-196. (Year: 2003).*
Agreda et al., 2013. Long-term stability of human genomic and human papillomavirus DNA stored in BD SurePath and Hologic PreservCyt liquid-based cytology media. Journal of clinical microbiology, 51(8), pp. 2702-2706. (Year: 2013).*
Bergallo, et al., 2006. Evaluation of six methods for extraction and purification of viral DNA from urine and serum samples. New Microbiologica, 29(2), pp. 111-119. (Year: 2006).*
Goldenberger, D., Perschil, I., Ritzier, M. and Altwegg, M., 1995. A simple"universal" DNA extraction procedure using SDS and proteinase K is compatible with direct PCR amplification. Genome Research, 4(6), pp. 368-370. (Year: 1995).*
Keegan, H., Boland, C., Malkin, A., Griffin, M., Ryan, F. and Lambkin, H., 2005. Comparison of DNA extraction from cervical cells collected in PreservCyt solution for the amplification of Chlamydia trachomatis. Cytopathology, 16(2), pp. 82-87. (Year: 2005).*
Daum et al. Detection and Molecular Characterization of Clinical Influenza A and B Viruses from Original Nasal Wash Specimens Preserved in Primestore® MTM. The 3rd European Conference of Influenza. Sep. (Year: 2008).*

Hagen, R.M., Gauthier, Y.P., Sprague, L.D., Vidal, D.R., Zysk, G., Finke, E.J. and Neubauer, H., 2002. Strategies for PCR based detection of Burkholderia pseudomallei DNA in paraffin wax embedded tissues. Molecular Pathology, 55(6), p. 398-400. (Year: 2002).*
Lee, T.H., Stromberg, R., Heitman, J., Tran, K. and Busch, M.P., 1994. Quantitation of residual white cells in filtered blood components by polymerase chain reaction amplification of HLA DQ-A DNA. Transfusion, 34(11), pp. 986-994. (Year: 1994).*
Muir, P., Nicholson, F., Jhetam, M., Neogi.S. and Banatvala, J.E., 1993. Rapid diagnosis of enterovirus infection by magnetic bead extraction and polymerase chain reaction detection of enterovirus RNA in clinical specimens. Journal of Clinical Microbiology, 31(1), pp. 31-38. (Year: 1993).*
Mania-Pramanik, J., Potdar, S. and Kerkar, S., 2006. Diagnosis of Chlamydia trachomatis infection. Journal of clinical laboratory analysis, 20(1), pp. 8-14. (Year: 2006).*
Dimulescu, I., Unger, E.R., Lee, D.R., Reeves, W.C. and Vernon, S.D., 1998. Characterization of RNA in cytologic samples preserved in a methanol-based collection solution. Molecular Diagnosis, 3(2), pp. 67-72. (Year: 1998).*
European Examination Report for Application No. EP10814484.1 dated Mar. 24, 2014.
European Examination Report for Application No. 10814484.1 dated Aug. 1, 2013.
Extended European Search Report for Appiication No. EP10814484 dated Dec. 13, 2012.
International Search Report, PCT/US2010/047653 dated May 30, 2011.
TriPath Imaging, SurePath® Collection Product Insert, (2009).
Draft Guidance for Industry and FDA Staff: Establishing the Performance Characteristics of In Vitro Diagnostic Devices for the Detention and Differentiation of Human Papillmaviruses, (2009), pp. 27.
Journal, of Inner Mongolia Agricultural University, vol. 21. No. 1, (Mar. 2000).
"HiPi Eco Taq polymerase manual manufactured by Elpis Biotech", 2008.
"Lysing solution manual", (Catalog No. 349202, Reference #23-1358,07, Feb. 2013), Feb. 2013.
Akane , Hydrogen Peroxide Decomposes the Hema Compound in Forensic Specimens and Improves the Efficiency of PCR, BioTechniques. 21, (1996), pp. 392-394.
BD , Material Safety Data Sheet for BD SurePath™ Preservative Fluid, (2011).
Berri, Mustapha, et al., "PCR-Based Detection of Coxilla burnetii from Clinical Samples", Methods in Molecular Biology vol. 216, (2003), pp. 153-161.
Bessetti, J , An introductioh to PCR inhibitors. Profiles in DNA, Promega Corporation, vol. 10, [online], [retrieved from internet an Apr. 10, 2015]<URL:http://www.promega.com/~/media/files/resources/profiles%20in%20dna/1001/an%20introduction%20to®20pcr%20inhibitors.pdf >. (Mar. 2007), pp. 9-10.
Burckhardt, J , "Amplification of DNA from whole blood." Genome Research, vol. 3, (1994), pp. 239-243.
Cattoreti, G , et al., "Antigen Unmasking on Formalin-fixed, Paraffin-Embedded Tissue Sections" Journal of Pathology, Chichesier, Sussex, GB, vol. 171, (1993), pp. 83-98.
Chan, K L, et al., "Revisiting ischemia and reperfusion injury as a possible cause of necrotizing enterocolitis: Role of nitric oxide and superoxide dismutase," Journal of Pediatric Surgery, vol. 37, No. 6 (Jun. 2002), (Jun. 2002), pp. 828-834.
De Roda Husman, Ana-Marie, et al., Journal of General Virology, 76:, (1995), pp. 1057-1062.
DiMulescu , et al., Characterization of RNA in cytologic samples preserved in a methanol-based collection solution. Molecular Diagnosis 3(2), (1998), pp. 67-72.
Dorris, Mark, PhD , Thesis: Reversing the Effects of Formalin Fixation, (1999), 9 pages.
Duval, Kristin , et al., Duval K, et al Optimized manual and automated recovery of amplifiable DNA from tissues preserved in buffered formalin and alcohol-based fixative. Forensic Sci Int Genet.;4(2). Epub Jul. 8, 2009, Feb. 2010, pp. 80-88.
Eisenbach , et al., Am Rev. Respir. Dis., 144, (1991), 1160-1163.

(56) References Cited

OTHER PUBLICATIONS

Englen, M.D. , et al., A rapid DNA isolation procedure for the identification of Campylobacter jejuni by the polymerase chain reaction, P-002688373, Letters in Applied Microbiology, 2000, 31, (2900), pp. 421-426.
Gilbert, M. Thomas, et al., "The Isolation of Nuclei Acids from Fixed, Paraffin Embedded Tissues—Which Methods Are Useful When?", PLoS ONE Issue 2(6): e537,(Jun. 20, 2007), pp. 1-12.
Howe, J. R., et al., "DNA extraction from parafin-embedded tissues using a salting-out procedure: a reliable method for PCR amlification of archival material", Histol. and Histopahtol vol. 12, (1997), pp. 595-601.
Hutchison , et al., "Macromolecule Synthesis in Yeast Spheroplasts." Journal of Bacteriology, vol. 94, No. 5. (Nov. 1967), pp. 1697-1705.
Keegan, Helen , et al., "Comparison of DNA Extraction from Cervical Cells Coiiecte in PreservCyt Solution for the Amplification of Chlamydia Trachomatis", Cytology 16, (2005), pp. 82-87.
Korbler, Tajana , et a., "A simple method fo RNA isolation from formalin-fixed and parafin-embedded lymphatic tissues", Experimental and Mol. Path. vol. 74, (2003), pp. 336-340.
Koumans , et al., Comparison of Methods for Detection of Chlamydia trachomatis and Neisseria gonorrhoeae Using Commercially Available Nucleic Acid Amplification Tests and a Liquid Pap Smear Medium. Journal of Clinical Microbiology 41(4), (2003), pp. 1507-1511.
Legrand, Beatrice , et al., "DNA genotyping of unbuffered formalin fixed paraffin embedded tissues". Forensic Science International vol. 125, (2002), pp. 205-211.
Masuda, Norikazu , et al., "Analysis of chemical: modification of RNA from formalin-fixed samples and optimization of molecular bilogy applications for such samples", Nucleic Acid Research vol. 27 (22). Sep. 27, 1999, 4436-4443.
Molina-Vila, Miguel , et al., "A Sensitive Method for Detecting EGFR Mutaitons in Non-small Cell Lung Cancer Samples with Few Tumor Cells", J. Thorac. Oncol., vol. 3, No. 11, Nov. 2008, pp. 1224-1235.
Pasternack , et al., Comparisonof Manual Amplicor PCR, Cobas Amplicor PCR, and LCx Assays for Detection of Chlamydia Trachomatis Infection in Women Using Urine Specimens. J Clin Microbiol; 35(2), (1997), pp. 402-405.
Persing , et al., Diagnostic Molecular Microbiology; Principles and Applications, Mayo Foundation, Rochester, MN Chapter 6, (1993).
Poljak, M , et al., Isolation of DNA from archival Papanicolaou stained cytological smears using a simple salting-out procedure. Clin Mol Pathol.; 48(1), Feb. 1995, M55-6.
Rait, Vladimir K, et al., "Modeling formalin fixation and antigen retrieval with bovine pancreatic ribonuclease A:I-Structural and functional alternations," Lab. Invest. vol. 4(3):, Mar. 2004), pp. 292-299.
Reizenstein , et al., Diagn. Microbiol. Infect. Disease, 17, (1993), pp. 185-191.
Rivero, Elena R.C., et al. Simple salting-out method for DNA extraction from formalin-fixed, paraffin-embedded tissues.Pathol Res Pract.; 202(7); Epub May 24, 2006, 2006, pp. 523-529.
Santos, Sara, et al., An efficient protocol for genomic DNA extraction from formalin-fixed paraffin-embedded tissues. Res Vet Sci.; 86(3); Epub Oct. 15, 2008, Jun. 2009, pp. 421-426.
Satiroglu-Tufan, N. , et al., "Rapid and effective DNA amplification by polymerase chain reaction directly from paraffin-embedded tissue", Aegean Path. J. vol. 1, (2004), pp. 33-38.
Sepp, R , et al., "Rapid techniques for DNA extraction from routinely processed archival tissue for use in PCR," J. Clin. Pathol. vol. 47:, (1994), pp. 318-323.
Shima , et al., "Poly-L-lysine produced by Streptomyces, Part II. Taxonomy and fermentation studies," Agricultural and Biological Chemistry, 45 (11), (1981), pp. 2497-2502.
Shin, J.H. , et al., Rapid Identification of Candida species in blood cultures by a clinically useful PCR Method. J Clin Microbial; 35(6), Jun. 1997, pp. 1454-1459.
Solomon, Mark J, et al., "Formaldehyde-mediated DNA-protein crosslinking: A probe for in vivo chromatin structures,"Proc. Natl. Acad. Sci. vol. 82, (Oct. 1983), pp. 6470-6474.
Tang , et al., Journal of Clinical Virology, 45:, (2009), S25-S28.
Thorpe. T.C., et al., BacT/Alert: An Automated Colormetric Microbial Detection System. J Clin Microbial, 28(7), Jul. 1990, pp. 1608-1612.
Ubukata, K , et al., Rapid Detection of the mecA gene in methicillin-resistant staphylococci by enzymatic detection of polymerase chain reaction products. J Clin Mirobial., Jul. 30, 1992, pp. 1728-1733.
Van Den Brule, Adriaan J.C., et al., Journal of Clinical Microbiology, 28(12), (1990), pp. 2739-2743.
Verkooyen, R.P. , et al., Detection of PCR inhibitors in cervical specimens by using the AMPLICOR Chlamydia trachomatis assay. Journal of Clinical Microbiology, vol. 34, No. 12, (1996), pp. 3072-3074.
Yursis, D , et al., Performance of the BD ProbeTec™ CT Qx and GC Qx Amplified DNA Assays with PreservCyt Specimens on the BD Viper™ System in Extracted Mode. Clinical Virology Symposium, (Year: 2008), Apr. 27, 2008, pp. 14.
Zeile, William L, et al., Vaccinia locomotion in host cells: Evidence for the universal involvement of actin-based motility sequences ABM-1 and AMB-2, Proceedings of the National Academy of Sciences, National Academy of Sciences, US. vol. 95, No. 23, Nov. 10, 1988, (Nov. 10, 1998), pp. 13917-13922, XP 002176723.
Zsikla, V. , et al., "Effect of buffered formalin on amplifcation of DNA from paraffin was embedded smal biopsies using real-time PCR", J. Clin. Pathol. 2004 vol. 57, (Sep. 20, 2015), pp. 654-656.
Examination Report dated Feb. 18, 2014 in Australian Patent Application No. 2010289430.
Examination Report dated Oct. 20, 2014 in Australian Patent Application No. 2010289430.
Examination Report dated Nov. 4, 2014 in European Patent Application No. 10814484.1.
Examination Report dated Jun. 24, 2015 in European Patent Application No. 10814484.1.
Examination Report dated May 31, 2016 in European Patent Application No. 10814484.1.
Examination Report dated Jan. 27, 2017 in European Patent Application No. 10814484.1.
Notice of Allowance dated Jun. 4, 2015 in Chinese Patent Application No. 2010800461347.
Notice of Allowance dated Jun. 10, 2015 in Australian Patent Application No. 2010289430.
Notice of Allowance dated Mar. 8, 2016 in Japanese Patent Application No. 2012528040.
Notice of Allowance dated May 22, 2017 in European Patent Application No. 10814484.1.
Notice of Allowance dated Nov. 7, 2017 in European Patent Application No. 10814484.1.
Notice of Allowance dated Sep. 18, 2019 in Canadian Patent Application No. 02772621.
Office Action dated Nov. 2, 2012 in Chinese Patent Application No. 2010800461347.
Office Action dated May 31, 2013 in Canadian Patent Application No. 02772621.
Office Action dated Sep. 10, 2013 in Chinese Patent Application No. 2010800461347.
Office Action dated Mar. 10, 2014 in Chinese Patent Application No. 2010800461347.
Office Action dated Sep. 19, 2014 in Canadian Patent Application No. 02772621.
Office Action dated Nov. 23, 2014 in Chinese Patent Application No. 2010800461347.
Office Action dated Jan. 13, 2015 in Japanese Patent Application No. 2012528040.
Office Action dated Nov. 10, 2015 in Japanese Patent Application No. 2012528040.
Office Action dated Jan. 18, 2016 in Canadian Patent Application No. 02772621.
Office Action dated Mar. 20, 2017 in Canadian Patent Application No. 02772621.

(56) References Cited

OTHER PUBLICATIONS

Office Action dated Mar. 8, 2018 in Canadian Patent Application No. 02772621.

* cited by examiner

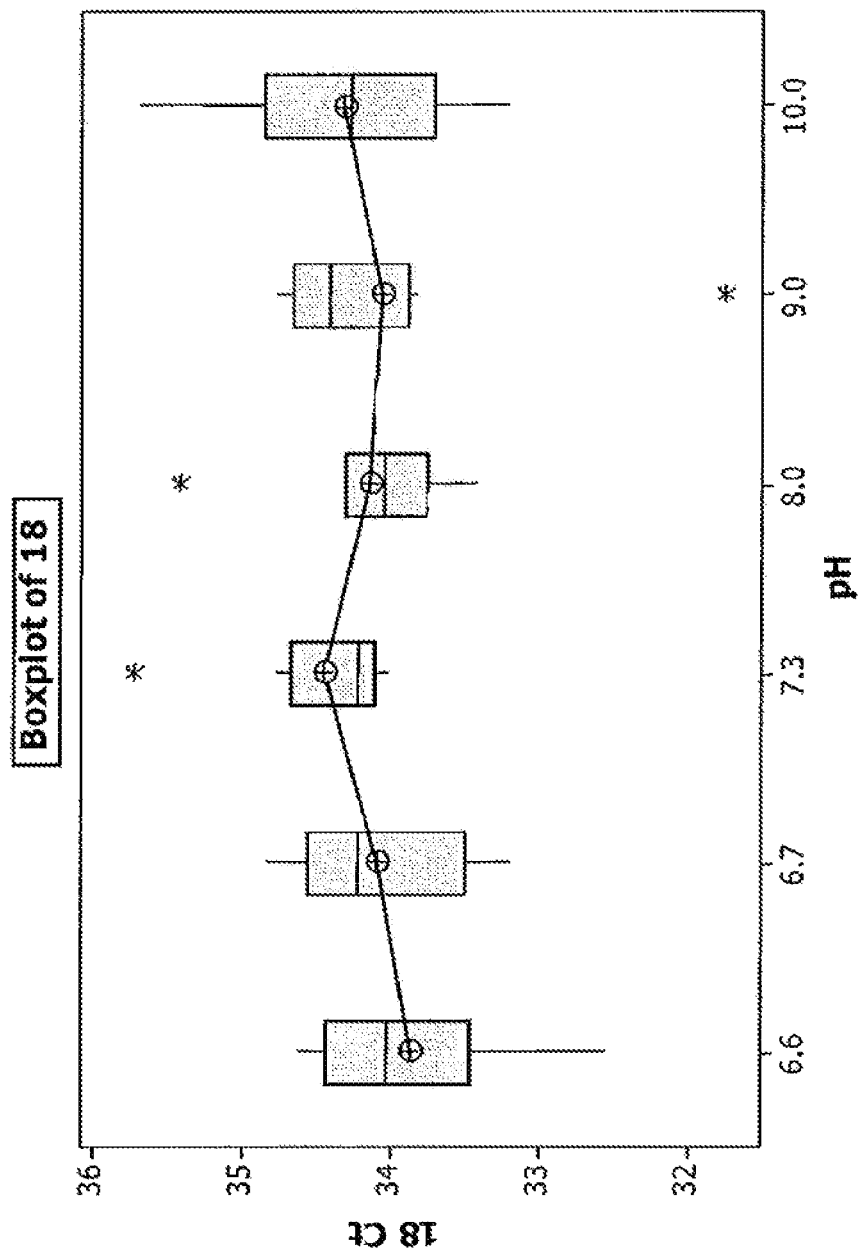

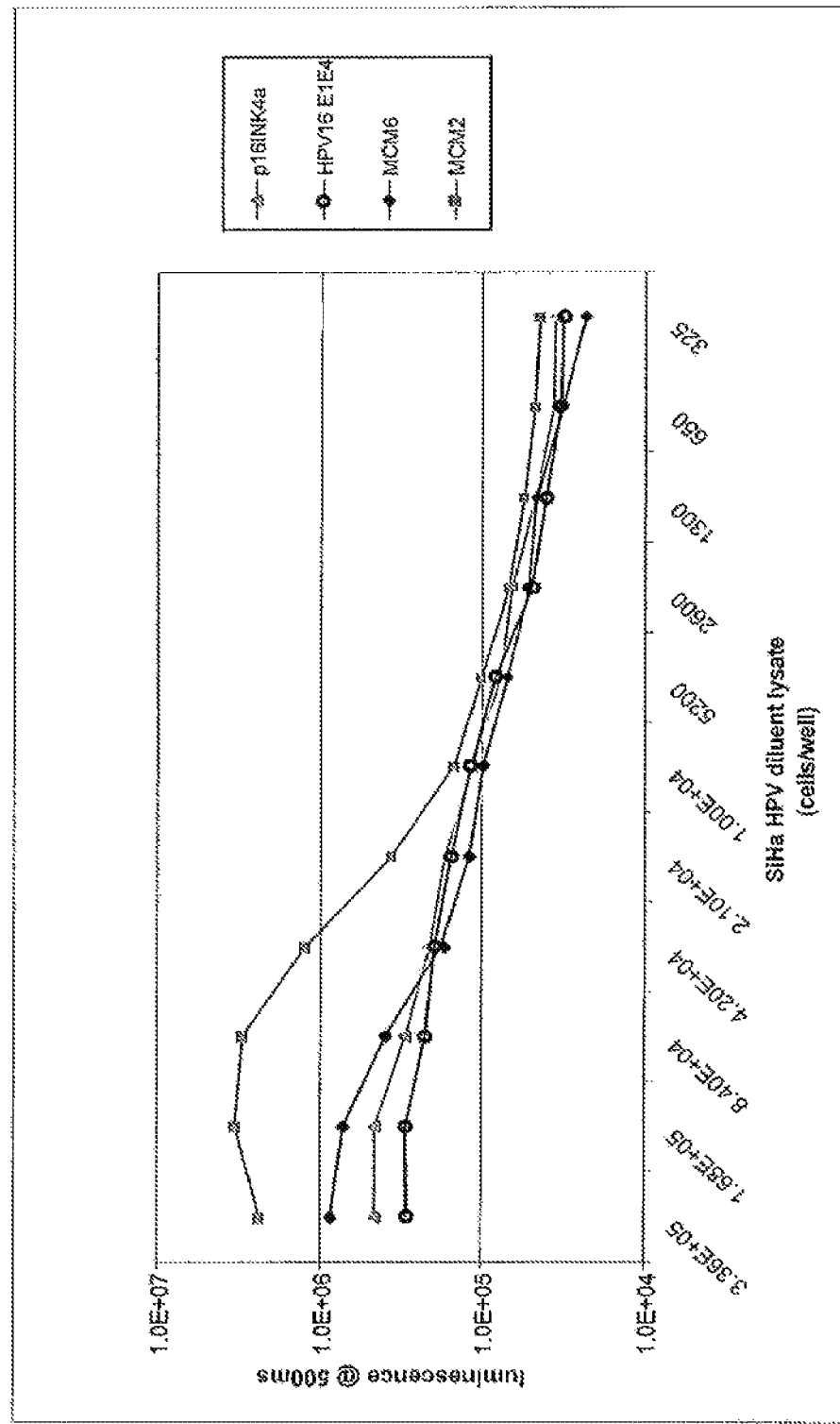
Figure 2. ELISA detection of protein biomarkers in SiHa cells resuspended in HPV diluent

METHODS AND COMPOSITIONS FOR DIRECT CHEMICAL LYSIS

CROSS REFERENCE TO RELATED APPLICATIONS

The present application is a continuation of U.S. patent application Ser. No. 15/067,428 filed on Mar. 11, 2016 which is a divisional application of U.S. patent application Ser. No. 12/874,602 filed on Sep. 2, 2010, and which issued as U.S. Pat. No. 10,190,152 on Jan. 29, 2019, which claims the benefit of U.S. Provisional Patent Application No. 61/239,553 filed Sep. 3, 2009, the disclosures of which are hereby incorporated herein by reference.

BACKGROUND OF THE INVENTION

The invention relates generally to methods and compositions for conducting diagnostic testing on preserved biological samples, and, in particular to performing nucleic acid extraction and amplification methods on such preserved samples.

In the fields of medical diagnosis and medical research, samples (e.g., tissues) are taken from a patient or subject (e.g. a human patient, a human subject, an experimental animal model of a human disease) to determine the condition of the subject in support of the research, determine the current condition of the patient for making a medical diagnosis, determine the response of the patient to a current course of therapy or treatment, etc.

Samples that are obtained for analysis, either for performing medical diagnosis or for use in scientific research, are often placed in a special transport/preservative medium to keep the sample from degrading or decomposing when removed from the subject. Thus, the sample will as closely as possible be in the exact condition it was in when removed from the subject. This ensures that the sample accurately reflects the state of the patient or subject at the time of sampling and will therefore yield the most accurate result in any subsequent studies of the sample. Some of these studies will involve nucleic acid (for example deoxyribonucleic acid (DNA) or ribonucleic acid (RNA)) extraction and amplification.

Extracting DNA and/or RNA from biological samples requires, among other steps, lysis of the cell wall (in the case of prokaryotic cells), lysis of the cell membrane (in the case of certain eukaryotic cells) or lysis of the viral capsid (in the case of viruses). Subsequent amplification requires, in part, the attachment of primers to specific sites within the target nucleic acid.

There are a number of protocols available for the extraction and subsequent amplification of nucleic acid. Some of these protocols utilize high throughput devices. High throughput devices are automatic in the sense that a sample is placed within the device together with appropriate chemicals and the extraction and amplification steps take place without further input from the operator (e.g. Viper™ XTR System by Becton Dickinson® BD ProbeTec $Q^x$ Amplified DNA Assay Package Insert, Becton Dickinson 2008). Other protocols utilize less sophisticated equipment and are typically referred to as manual procedures. However, regardless of the protocol, the need to lyse the cells or viral capsids in order to release the nucleic acid, the need to attach the nucleic acid to particles such as ferric oxide in order to extract the nucleic acid from the rest of the sample, and the need to attach primers to the target nucleic acid in order to amplify the nucleic acid remain.

Transport media (e.g. liquid cytology media) typically contains one or more constituents that preserve certain cells in one or more ways (e.g., prevent the breakdown of the cell wall or the cell membrane by cell lysis). In addition, some of these constituents serve the dual purpose of preservation and decontamination of the sample. These constituents are known to interfere with the ability to lyse cell membranes and walls, the ability for the extracted nucleic acids to attach to particles utilized in nucleic acid extraction, and the ability to amplify target nucleic acid.

Liquid based cytology compositions such as SurePath® (Tripath Imaging, Inc., N.C.) solution or ThinPrep® PreservCyt® solution (Hologic Inc., MA), adversely affect the ability to extract amplifiable target nucleic acid from samples exposed thereto. Many reasons have been suggested to explain this observed adverse effect including: 1) degradation of the nucleic acids by constituents in the media; 2) chemical alteration of the nucleic acids by constituents in the media; and 3) inhibition of the cell lysing mechanism in the tissue, which inhibits the release of the nucleic acids for extraction and amplification. In order to avoid the adverse effects of the liquid cytology compositions on extracted DNA, cells are extracted from the compositions prior to lysis. Typically, the extraction requires centrifugation to decant the liquid cytology composition from the cells. The cells are then resuspended in a buffer and lysed with an enzyme. Such extra steps are not typically compatible with many high throughput automatic devices such as, for example, the aforementioned Viper™ System. Even in situations where automation is not involved, such steps are nevertheless time-consuming. The additional time required by these steps can delay obtaining the test results and is preferably avoided.

One example of a media kit for purification of nucleic acids is the QIAamp MinElute Media Kit from Qiagen. This media kit is described in the QIAmp MinElute Media Handbook dated February, 2004. The QIAamp procedure is described as having 4 steps: lyse, bind, wash and elute. In this procedure, the samples are lysed using proteinase K followed by binding the nucleic acids to the QIAmp MinElute column by absorption onto the silica-gel lysate. Although the QIAamp procedure is a proven method, it is optimized for the purification of only 250 µl of liquid cytology media and is both labor intensive and time consuming (i.e. it requires 18 steps that includes 65 minutes of different temperature incubations, 5 centrifugation steps, 2 vacuum filtration steps and several mixing steps). The use of such multi-step methods has heretofore been required to successfully purify nucleic acids from fixed samples such as liquid cytology media and paraffin embedded tissue. It is well known that purification of nucleic acids from fixed media is more difficult than from fresh tissue because the fixatives in the media introduce undesirable chemical modifications of the target molecules in the sample. The reactions can occur to crosslink or otherwise modify nucleic acids in a sample. Other additives in the transport media can also cause undesired cross-linking. For example, cross-linking due to the presence of formalin in the transport media is described in Rai, V. K., et al., "Modeling formalin fixation and antigen retrieval with bovine pancreatic ribonuclease A:I-Structural and functional alterations," *Lab. Invest.* Vol. 84(3):292-299 (March 2004). Formaldehyde also produces cross-linking between nucleic acids and proteins as described in Solomon, M. J., "Formaldehyde-mediated DNA-protein crosslinking: A probe for in vivo chromatin structures," *Proc. Natl. Acad. Sci.* Vol. 82, pp. 6470-6474 (October 1983). As described in Sepp, R., et al. "Rapid techniques for DNA extraction from routinely processed archival tissue for use in PCR," *J. Clin. Pathol.* Vol. 47:318-323 (1994), DNA extraction from cells taken from formalin-fixed paraffin wax typically requires processing steps (e.g. prolonged boiling) that can adversely affect the amount of DNA for amplification. According to Sepp, R., et al. boiling the sample is needed to, among other things, inactivate the proteinase K. Furthermore, proteinase K is inhibited by the constituents in many fixatives making its direct use of limited effectiveness in breaking down protein cross-links.

Therefore, methods and compositions for extracting DNA from tissues and other cells and cell components that overcome the problems of cross-linking and other undesired modifications to nucleic acid yet do not require prolonged high temperature processing that can adversely affect the sample or make the process more expensive and time consuming continue to be sought.

SUMMARY OF THE INVENTION

A direct chemical lysis composition for combination with a specimen storage composition includes an assay compatible buffer composition and an assay compatible surfactant. Such compositions prevent undesired modifications to nucleic acid lysed from cells in the biological sample and assays of samples from such compositions do not require expensive and time-consuming steps such as centrifugation and prolonged high temperature processing.

The direct chemical lysis composition of the present invention permits direct nucleic acid extraction from the cells in the biological sample without the need to decant off the cytology media or otherwise exchange the cytology media with assay compatible buffers. Cell lysis can occur directly when the sample is still combined with the direct chemical lysis composition. There is no need to combine the sample with proteinase K or some other enzyme to extract nucleic acids from the cells.

In one embodiment, the direct chemical lysis composition is deployed as an additive to a liquid based cytology (LBC) composition that is used for sample dilution, storage, transportation, etc. The direct chemical lysis composition allows for sample lysis as the sample is being pre-warmed or incubated prior to NA extraction from the sample. Examples of LBC include, but are not limited to, SurePath LBC and ThinPrep PreservCyt LBC.

In one embodiment, the direct chemical lysis composition for combination with a specimen storage composition has an assay compatible buffer composition and an assay compatible surfactant. In preferred embodiments, the assay compatible buffer composition has a buffer component and a metal salt component. In a preferred embodiment, the pH of the direct chemical lysis composition is in the range of about 6.6 to about 10.

Examples of suitable metal salts include sodium chloride (NaCl), potassium chloride (KCl), sodium acetate ($C_2H_3NaO_2$) and ammonium sulfate (($NH_4$)$_2SO_4$). In the described embodiment, the concentration of the metal salt in the direct chemical lysis composition is at least about 0.01 M. Preferably the salt is NaCl and the salt concentration is in the range of about 0.01 M to about 1 M.

In preferred embodiments, the buffer component concentration is in the range of about 0.2 M to about 2M. Examples of suitable buffer components include tris(hydroxymethyl) amino methane and the acid salt of tris(hydroxymethyl) amino methane.

In certain embodiments, the direct chemical lysis composition also contains a non-ionic surfactant. Examples of suitable surfactants include polyethylene glycol based non-ionic surfactants such as polyethylene glycol octylphenyl ether (commercially available as Triton® x-100). Additional examples of suitable non-ionic surfactants include polysorbate surfactants such as polyoxyethylene (20) sorbitan monolaurate (known commercially as polysorbate 20 or Tween® 20). Both Tween® 20 and Triton® x-100 are commercially available. In preferred embodiments, the concentration of the non-ionic surfactant is in the range of about 0.01 to about 2 percent (v/v).

In certain embodiments, the directed chemical lysis composition also includes glycine.

In one preferred embodiment the buffer component is the acid salt of tris(hydroxymethyl)amino methane and the buffer component concentration is about 0.75 M, the NaCl concentration is about 0.19 M and the polyethylene glycol octylphenyl ether concentration is about 0.75 percent (v/v).

The present invention also contemplates a method for analyzing samples stored in a specimen storage composition. In the method, a sample is combined with a direct chemical lysis composition as described above. At least a portion of the sample is removed from the specimen storage composition along with at least some of the specimen storage composition. The sample combined with the specimen storage composition is then incubated at a temperature of at least 80° C. for a time sufficient to lyse at least a portion of the cells in the removed portion of the sample. The nucleic acid is extracted from the sample and then amplified. Extraction can occur using either an automated or a manual process. In certain embodiments the target nucleic acid is either RNA or DNA. For example, the sample is cells selected from the group consisting of vaginal cells, cervical cells, endocervical cells, anal cells, exfoliated cells, oral cells, throat cells and peritoneal cells.

In one embodiment the sample is combined with a direct chemical lysis composition comprising a) an assay compatible buffer composition; and b) an assay compatible surfactant. At least a portion of the sample is removed from the specimen storage composition wherein the removed portion also includes the specimen storage composition. The removed portion of the sample is incubated at a temperature that is at least 80° C. for a time sufficient to lyse at least a portion of the cells in the removed portion of the sample. The nucleic acid is extracted and amplified as described above. In this embodiment the removed portion of the sample is not further separated from the specimen storage medium prior to the steps of lysing and extraction. The extraction steps can be either manual or automated.

Other embodiments of the present invention include a diagnostic kit for extracting, by direct chemical lysis, nucleic acids from a specimen removed from a specimen storage composition. The diagnostic kit includes the direct chemical lysis composition described above. The specimen storage composition is provided to preserve a tissue sample.

In one embodiment, the diagnostic kit for extracting nucleic acids includes a specimen storage composition with a direct chemical lysis composition having: a) an assay compatible buffer component; and b) a non-ionic surfactant, wherein the specimen storage is provided to preserve a tissue sample. The assay compatible buffer composition has a buffer component and a metal salt. In one embodiment, the metal salt is NaCl and the concentration of NaCl in the direct chemical lysis composition is at least about 0.01 M and the buffer component concentration is in the range of about 0.2 M to about 2M. The pH of the direct chemical lysis composition is in the range of about 7 to about 9 and the concentration of the non-ionic surfactant is in the range of about 0.01 to about 2 percent (v/v).

BRIEF DESCRIPTION OF THE DRAWINGS

FIGS. 1A-D illustrate the effect of pH on the efficiency of one embodiment of the direct chemical lysis composition.

FIG. 2 illustrates protein biomarker detection from samples lysed using one embodiment of the direct chemical lysis composition and method disclosed herein.

DETAILED DESCRIPTION

Figure 1A:
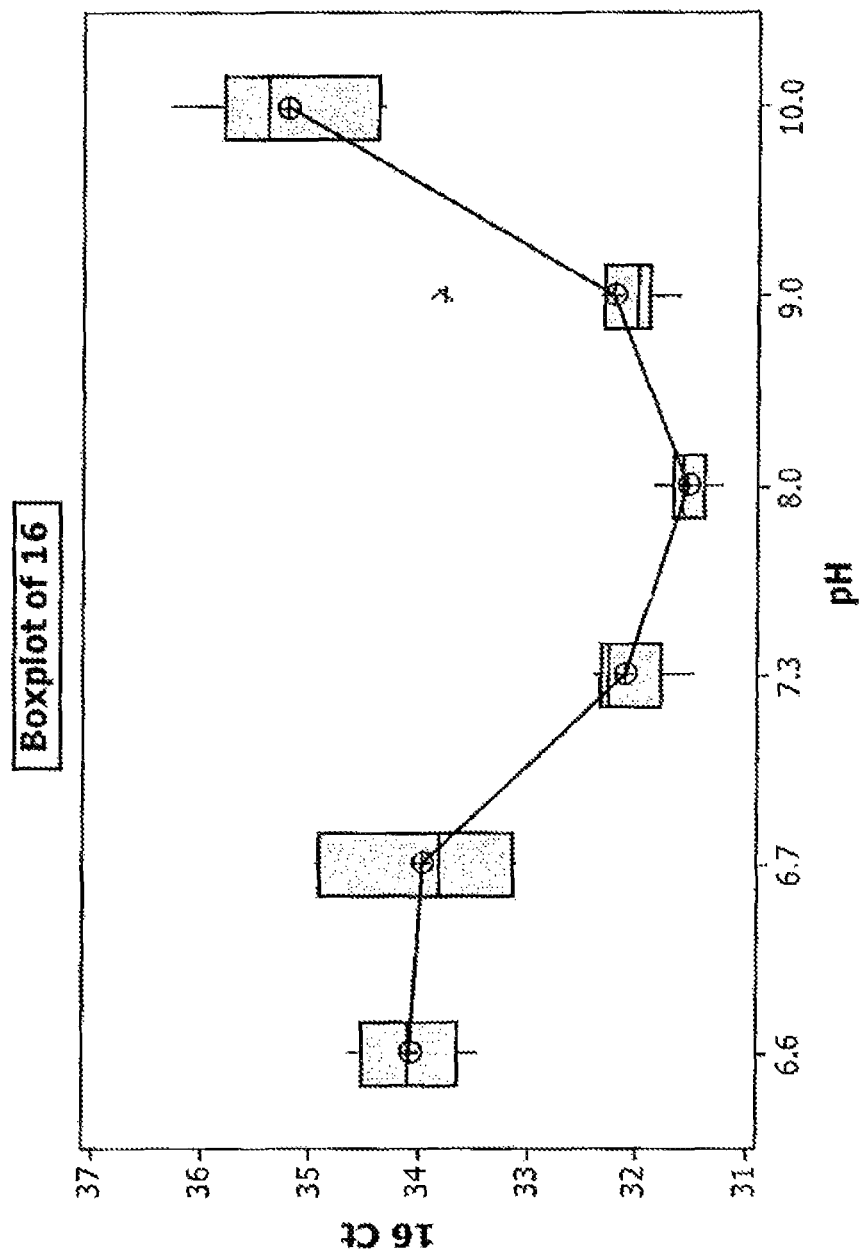

Before explaining at least one embodiment of the invention in detail, it is to be understood that the invention is not limited in its application to the details set forth in the following description or exemplified by the examples. The invention is capable of other embodiments or of being practiced or carried out in various ways. Also, it is to be understood that the phrasing and terminology employed herein is for the purpose of description and should not be regarded as limiting. The following are definitions of certain terms used in this specification.

A direct chemical lysis composition is a composition that allows for lysis of the cellular components in the sample for nucleic acid (NA) extraction thereof without the need for intervening steps to separate the chemical lysis composition from the sample. The direct chemical lysis composition also allows for the assay/detection of other sample constituents (e.g. protein biomarkers) without the need to separate the chemical lysis composition from the sample prior to assay/detection of those constituents.

Examples of NA are single or double-stranded DNA and RNA. Further examples of NA that can be extracted by the method include not only genomic DNA or RNA from animals, plants, bacteria, viruses, fungi and parasitic organisms, but also the DNA or RNA of mitochondria or chloroplasts. Examples of other classes of NA that can be extracted by the method include not only mRNA, but also transfer RNA, ribosomal RNA, and small nuclear RNA as well as plasmid DNA. DNA and RNA extracted by the method of the invention may also be either wholly or partially single-stranded or possess other tertiary or quaternary structure. A sample containing NAs is exemplified by viable samples such as leukocyte cells, the culture of host cells containing vectors or the like that are typically prepared by gene recombinant technology, cells infected with viruses or phages, viruses in blood, and the culture of a sample microorganism. The culture may contain microorganisms but its supernatant alone is sufficient. Not only an artificial culture but also a naturally occurring culture is applicable. In case of a sample containing lumps of microorganism, homogenization or sonication may be performed as required to achieve good efficiency of extraction.

Alternative sample types include but are not limited to biological specimens for the diagnosis of infectious or non-infectious diseases, environmental specimens, or samples of food or water. The target NA may be a particular sequence or it may be a class of NA. A class of nucleic acid is, for a particular assay method, those molecules of NA whose chemical, physical or biological properties are such that they can be expected to be extracted effectively in methods used for NA extraction. Typically, but not necessarily, the NA of a class are all DNA or DNA analogs or all RNA or RNA analogs. Other targets may be protein sequences such a protein biomarkers.

Targeted organisms can include but are not limited to *Chlamydia trachomatis, Neisseria gonorrhoeae*, Human Papilloma Virus, Human Immunodeficiency Virus 1/2, Hepatitis C Virus, Hepatitis B Virus, Severe Acute Respiratory Syndrome Virus, Influenza A/B, Herpes Simplex Viruses 1-6, Enteroviruses, West Nile Virus, Parainfluenza viruses, Adenoviruses, Respiratory Syncytial Virus A/B, *Mycobacterium* paratuberculosis, *Mycobacterium avium*-intracellular complex, *Mycobacterium tuberculosis* complex, Cytomegalovirus, Group B *Streptococcus, Bordetella pertussis*, and *Bordetella* Para pertussis.

In one aspect of the invention, the target nucleic acid is a particular RNA or cDNA from one or more of the following sources: bacterial pathogens, bacterial non-pathogens, viral pathogens, viral non-pathogens, fungal pathogens, fungal non-pathogens, yeast pathogens, yeast non-pathogens, parasitic pathogens, parasitic non-pathogens, plants, animal products, food, total RNA or cDNA within the sample matrix, total prokaryotic RNA or cDNA, total eukaryotic RNA or cDNA, or total viral RNA or cDNA.

In another aspect of the invention, the target nucleic acid sought is DNA from one or more of the following sources: bacterial pathogens, bacterial non-pathogens, viral pathogens, viral non-pathogens, fungal pathogens, fungal non-pathogens, yeast pathogens, yeast non-pathogens, parasitic pathogens, parasitic non-pathogens, plants, animal products, food, total DNA within the sample matrix, total genomic prokaryotic DNA, total genomic eukaryotic DNA, or total viral DNA.

In another aspect of the invention, the target is a protein biomarker.

A specimen storage composition is any composition that is used to store and or transport a biological sample prior to the extraction of nucleic acid from the cellular components in the sample. As noted above, specimen storage compositions include LBC media, paraffin media, etc. In one example the specimen storage composition has at least one constituent selected from the group consisting of formaldehyde, formic acid, methanol, ethanol, buffered formalin, and EDTA.

Assay compatible as used herein is any composition that will not significantly adversely affect that assay to which the samples (e.g., extracted nucleic acid/proteins) are subjected. For example, an assay compatible composition will not modify the extracted nucleic acid in the sample in a manner that will adversely affect the ability of the downstream assay to detect the nucleic acid or other sample constituents such as protein biomarkers.

In one embodiment, the direct chemical lysis composition described herein has a two-component assay compatible buffer composition. The assay compatible buffer composition will not modify the extracted nucleic acid in the sample in a manner that will adversely affect the ability of the downstream assay to detect the nucleic acid either by itself or when combined with other constituents of the chemical lysis composition or with constituents of the extracted nucleic acid (e.g. remnants of the specimen storage composition). The first component of the assay compatible buffer composition is an assay compatible buffer. Such buffers are well known to one skilled in the art and are not listed exhaustively herein. Examples of suitable buffers include tris(hydroxymethyl)amino methane and the acid salt of tris(hydroxymethyl)amino methane (Tris HCl herein). The final working concentration of the buffer in the direct chemical lysis composition is in range of about 0.2 M to about 2 M. Preferably the concentration of the buffer component is about 0.5 M to about 1 M. All concentrations herein are expressed as final working concentrations (i.e. concentrations at which the direct chemical lysis composition is combined with the sample).

The second component of the assay compatible buffer is a salt. Examples of suitable salts include NaCl, KCl, $C_2H_3NaO_2$ (sodium acetate) and $(NH_4)_2SO_4$ (ammonium sulfate). In preferred embodiments the salt is a metal salt and, most preferably, NaCl. The concentration of the salt in the direct chemical lysis composition is in the range of about 0.01 M to about 1 M. In preferred embodiments, the concentration of the metal salt is about 0.1 M to about 0.5 M and most preferably about 0.1 M to about 0.4 M. The salt concentration in a particular direct chemical lysis composition depends upon the buffer, pH and surfactants (if any) in the composition.

The direct chemical lysis composition also contains an assay compatible surfactant. Examples of suitable surfactants include the above-described Triton® X-100 and Tween® 20 (polysorbate 20). Assay compatible is as defined above. In a preferred embodiment, the assay compatible surfactant is a polyethylene glycol based non-ionic surfactant. The concentration of the non-ionic surfactant is in the range of about 0.01 to about 2 percent (v/v). In preferred embodiments, the non-ionic surfactant is polyethylene glycol octylphenyl ether. Assay compatible surfactants are well known to those skilled in the art and are not discussed in detail here.

The direct chemical lysis composition has a pH in the range of about 6.6 to about 10. In preferred embodiments the pH is in the range of about 7 to about 9.

The direct chemical lysis composition described herein facilitates nucleic acid extraction from media-fixed samples by reducing the cross-linking that typically occurs between the NA and the media constituents to provide NA that is both extractable and amplifiable. In one embodiment, a sample is combined with the direct chemical lysis and incubated at a temperature in the range of about 100° C. to about 130° C. and for a time in the range of about 10 minutes to about 30 minutes to chemically lyse at least a portion of the cells and, to the extent NA cross-linking has occurred, de-crosslink the NA. This is followed by extraction of the NA from the sample. In preferred embodiments, the NA is DNA and DNA extraction is accomplished via magnetic separation of the DNA using ferric oxide particles. In preferred embodiments, the extraction protocol is compatible with the BD Viper XTR™ platform. Such a protocol provides for binding the DNA to the ferric oxide particles, washing the rest of the sample from the particles and eluting the DNA from the particles. The extracted DNA is the subjected to a suitable amplification and detection assay (e.g. real time PCR).

In another embodiment, the sample is analyzed for target antigens (e.g. protein biomarkers). Conventional assays for detecting antigens extracted from a sample are well known to one skilled in the art and are not described in detailed herein. In one example, antibody capture molecules are used to bind and assay target antigens. Antibody methods for such capture are routinely used in a variety of different formats. One of the most commonly practiced techniques is the Enzyme Linked Immunosorbent Assay (ELISA) which is routinely used in protein diagnostic applications. A desired characteristic of protein detection methods is the ability to both preserve and retrieve antigens from a cell such that they can be exposed to the capture antibody and also in some cases retain their native shape and allow conformationally-dependent antibodies to specifically bind to the target antigen. Another desired characteristic is the ability to permit the selective binding of the correct antibody molecules to the target and allow non-specific interactions to be removed during the wash steps. Protein biomarker detection therefore requires that the assay compatible buffer be compatible with and facilitate specific protein binding interactions. The direct chemical lysis composition described herein is sufficiently strong to lyse the cells, thereby liberating the protein contents of those cells. The direct chemical lysis composition does not adversely affect the liberated proteins, and protects the proteins from proteolytic enzymes. Finally, the assay compatible buffer is compatible with specific antibody binding and does not interfere with this process due to denaturing effects, ionic interactions etc.

The following are provided some examples to specifically illustrate the concepts described above. The following examples are highly specific embodiments of the present invention and are not to be construed as limiting the invention in any way, except in a manner consistent with the appended claims.

Example 1. Extraction of HPV DNA from a Patient Sample Stored in SurePath LBC

Two solutions were compared to determine their efficacy as direct chemical lysis compositions. The first was a diluent that contained 1M Tris-HCl, 0.5M NaCl, 1% Triton X-100 and had a pH of 9.0 (Diluent 1 herein). The second diluent contained 330 mM Tris-HCl, 16.67 mM NaCl and had a pH of 7.8 (Diluent 2 herein). Stock patient-derived cells were harvested and stored in SurePath LBC for 21 days. Both Diluent 1 and Diluent 2 are embodiments of the direct chemical lysis composition of the present invention.

Specifically, stock patient-derived cells were diluted in SurePath LBC at a concentration of about 12,500 cells/ml. Forty-eight sample tubes were prepared for assay on the Becton Dickinson (BD) Viper™ tool. Twenty-four tubes had 0.85 ml of Diluent 1 and twenty-four had the same amount of Diluent 2. Diluted patient-derived cells (0.25 ml) were added into each of the 48 sample tubes. After combining with the samples, the final working buffer concentrations were as follows: i) 0.77M Tris-HCl, 0.386M NaCl, 0.77% Triton X-100 (with a pH of approximately 9.0) in Diluent 1; and ii) 0.255M Tris-HCl, 0.0129M NaCl (with a pH of approximately 7.8) in Diluent 2.

Eight samples from each group of twenty-four were incubated either at i) room temperature, ii) 80° C., or iii) 120° C., all for twenty minutes. The samples were then cooled for twenty-five minutes at room temperature. The samples were then subjected to a modified Viper™ XTR DNA extraction protocol using iron oxide (FEO) particles and 0.8 ml of the pre-warmed or incubated sample was used for extraction. The extraction protocol for Viper™ XTR is commercially available and not described in detail herein. To the extent DNA was extracted, DNA for the sample was eluted in 400 µl elution/neutralization buffer. The eluate (20 µl) was mixed with 5 µl of PCR master mix, and 20 copies/reaction of HPV 18 and HPV 45 plasmid DNA targets were post-spiked into each reaction for test of PCR inhibition. The real-time PCR assays were used for detection of HPV 16, 18 and 45, and human DNA endogenous control gene HBB. DNA detection was determined by the resulting cycle threshold (Ct) values. The Ct values less than about 30 represent strong positive reactions indicative of abundant target nucleic acid in the samples. Ct values of 30-35 represent moderate to low positive reactions indicative of moderate to low amounts of target nucleic acid in the sample. Ct values of 35-45 represent weak reactions that indicate minimal amounts of target nucleic acid in the sample. Ct values above about 45 are expressed as "No Ct", indicating that no DNA was being detected.

TABLE 1

Extraction of HPV DNA from Patient Samples stored in SurePath media

|  | Diluent 2 | | | Diluent 1 | | |
| --- | --- | --- | --- | --- | --- | --- |
|  | RT | 80° C. | 120° C. | RT | 80° C. | 120° C. |
| HPV16 | | | | | | |
| 1 | No Ct | No Ct | 32.57 | No Ct | 36.97 | 31.20 |
| 2 | No Ct | No Ct | 32.49 | No Ct | No Ct | 30.56 |
| 3 | No Ct | No Ct | 32.33 | No Ct | No Ct | 30.40 |
| 4 | No Ct | No Ct | 32.55 | No Ct | No Ct | 30.34 |
| 5 | No Ct | No Ct | 32.88 | No Ct | No Ct | 30.65 |
| 6 | No Ct | No Ct | 32.57 | No Ct | 36.99 | 30.54 |
| 7 | 36.73 | No Ct | 32.35 | No Ct | No Ct | 30.94 |
| 8 | No Ct | No Ct | 32.64 | No Ct | No Ct | 30.56 |
| AVG. |  | | 32.55 | | | 30.65 |
| HPV45 | | | | | | |
| 1 | 33.88 | 33.08 | 32.87 | 32.90 | 33.49 | 33.37 |
| 2 | 33.61 | 33.34 | 32.67 | 33.86 | 29.31 | 33.09 |
| 3 | 33.85 | 34.38 | 33.92 | 33.39 | 32.96 | 32.80 |
| 4 | 34.14 | 33.54 | 33.47 | 33.46 | 35.02 | 33.14 |
| 5 | 34.26 | 34.11 | 33.60 | 32.10 | 34.39 | 33.64 |
| 6 | 33.18 | 33.58 | 33.64 | 32.98 | 33.73 | 33.71 |
| 7 | 33.39 | 33.35 | 34.08 | 33.11 | 32.92 | 33.18 |
| 8 | 33.44 | 33.86 | 34.04 | 33.60 | 33.92 | 32.69 |
| AVG. | 33.72 | 33.66 | 33.54 | 33.18 | 33.22 | 33.20 |
| HBB | | | | | | |
| 1 | No Ct | No Ct | 37.91 | No Ct | 42.51 | 34.85 |
| 2 | No Ct | No Ct | 38.68 | No Ct | 41.67 | 35.48 |
| 3 | No Ct | No Ct | 37.48 | No Ct | No Ct | 34.34 |
| 4 | No Ct | No Ct | 37.25 | No Ct | No Ct | 34.95 |
| 5 | No Ct | No Ct | 37.16 | No Ct | No Ct | 34.9 |
| 6 | No Ct | No Ct | 37.88 | No Ct | No Ct | 35.48 |
| 7 | No Ct | No Ct | 39.14 | No Ct | No Ct | 35.22 |
| 8 | No Ct | No Ct | 36.99 | No Ct | No Ct | 34.99 |
| AVG. | | | 37.80 | | | 35.03 |
| HPV18 | | | | | | |
| 1 | 34.55 | 34.77 | 34.78 | 34.37 | 34.08 | 34.03 |
| 2 | 33.73 | 34.12 | 34.25 | 34.60 | 34.33 | 33.82 |
| 3 | 34.59 | 33.97 | 34.00 | 34.05 | 33.77 | 33.44 |
| 4 | 34.47 | 34.53 | 33.78 | 33.78 | 34.68 | 33.52 |
| 5 | 34.84 | 34.87 | 33.86 | 34.36 | 34.17 | 33.41 |
| 6 | 33.99 | 33.63 | 34.82 | 33.61 | 33.86 | 34.74 |
| 7 | 33.77 | 34.68 | 34.00 | 34.05 | 33.47 | 33.42 |
| 8 | 33.84 | 34.24 | 34.11 | 34.57 | 34.79 | 33.99 |
| AVG. | 34.22 | 34.35 | 34.20 | 34.17 | 34.14 | 33.80 |

Incubation in Diluent 1 at 120° C. reduced the Ct value of HPV 16 and HBB by 1.90 and 2.77 respectively when compared with incubation in Diluent 2 at 120° C. Incubation at room temperature or 80° C. in both diluents gave no amplification for HPV16 and HBB. The detection of spiked HPV 45 and HPV 18 confirmed that the assay itself worked but that HPV16 and HBB were not detected at lower incubation temperatures, indicating that lysis, extraction or detection did not occur in these samples.

Example 2. Extraction of HPV DNA from SurePath Using Different Diluents and Individual Diluent Components Stock patient-derived cells were diluted in SurePath LBC at 12500 cells/ml. Forty-eight BD Viper sample tubes were prepared. There were eight tubes in each group, with six groups (a-f) total. In each group 0.85 ml of one of the following buffers were added:

a. 1M Tris, (pH 9.0) only;
b. 0.5M NaCl;
c. 1% Triton X-100;
d. a+b+c;

Diluted patient cells (0.25 ml) were added to each of the 48 sample tubes. After combining with the samples, the final working buffer concentrations were as follows: 0.77M Tris-HCl in group a; 0.386M NaCl for group b; 0.77% Triton X-100 in group c; and 0.77M Tris-HCl, 0.386M NaCl, and 0.77% Triton X-100 in group d (the combination of buffers of a, b, and c). All sample tubes were incubated at 120° C. for 20 min. The samples were then cooled for 25 minutes to room temperature. The samples were then loaded onto the BD Viper™ XTR tool and 0.8 ml was used for extraction as describe above. DNA was eluted from the samples in 400 µl elution/neutralization buffer. Eluate (20 µl) was mixed with 5 µl of PCR master mix. Twenty copies/reaction of HPV 18 and HPV 45 plasmid DNA targets were post-spiked into each reaction as a control to test of PCR inhibition. The real-time PCR assays were used for detection of HPV 16, 18 and 45, and human DNA endogenous control gene HBB.

TABLE 2

Extraction of HPV DNA from SurePath LBC media using HPV diluents and individual component buffer

|  | 1M Tris (a) | 0.5M NaCl (b) | 1% Triton (c) | a + b + c |
| --- | --- | --- | --- | --- |
| HPV16 | | | | |
| 1 | 35.27 | 35.86 | 34.56 | 32.43 |
| 2 | 37.07 | 36.62 | 36.55 | 31.03 |
| 3 | 34.27 | No Ct | 36.68 | 31.30 |
| 4 | 34.52 | No Ct | 35.65 | 30.95 |
| 5 | No Ct | No Ct | 34.37 | 31.62 |
| 6 | 35.90 | No Ct | 33.71 | 31.21 |
| 7 | 34.26 | No Ct | 34.46 | 31.20 |
| 8 | 34.09 | 35.66 | 35.12 | 30.80 |
| AVG. | 35.05 | 36.05 | 35.14 | 31.33 |
| HPV45 | | | | |
| 1 | 33.47 | 34.61 | 34.19 | 35.22 |
| 2 | 33.76 | 34.17 | 33.90 | 33.39 |
| 3 | 34.01 | 33.56 | 34.01 | 33.69 |
| 4 | 33.80 | 31.61 | 34.29 | 33.98 |
| 5 | 33.01 | 32.86 | 33.23 | 33.57 |
| 6 | 32.59 | 33.49 | 33.44 | 33.43 |
| 7 | 33.37 | 32.56 | 33.44 | 33.05 |
| 8 | 32.75 | 33.25 | 35.33 | 33.92 |
| AVG. | 33.35 | 33.26 | 33.98 | 33.78 |
| HBB | | | | |
| 1 | No Ct | No Ct | No Ct | 42.35 |
| 2 | No Ct | No Ct | No Ct | 44.25 | 41.29 |
| 3 | No Ct | No Ct | 43.81 | 40.94 |
| 4 | No Ct | No Ct | No Ct | 40.38 |
| 5 | No Ct | No Ct | No Ct | 41.67 |
| 6 | 43.34 | No Ct | 42.17 | 40.63 |
| 7 | 44.52 | No Ct | 44.87 | 41.02 |
| 8 | No Ct | No Ct | No Ct | 40.70 |
| AVG. | 43.93 |  | 43.78 | 41.12 |
| HPV18 | | | | |
| 1 | 34.99 | 34.94 | 34.05 | 34.34 |
| 2 | 33.94 | 34.56 | 33.84 | 34.18 |
| 3 | 34.80 | 34.68 | 34.65 | 34.27 |
| 4 | 33.97 | 34.52 | 33.80 | 33.74 |
| 5 | 33.95 | 35.75 | 33.89 | 34.25 |
| 6 | 35.17 | 33.90 | 34.27 | 34.35 |
| 7 | 34.39 | 34.56 | 34.41 | 33.64 |
| 8 | 33.87 | 34.94 | 34.03 | 34.32 |
| AVG. | 34.38 | 34.73 | 34.12 | 34.14 |

HPV types 16, 18 and 45 were detected using d) above with incubation at 120° C. The other individual diluent components (1M Tris, 0.5 M NaCl and 1% Triton) did not provide for consistent DNA detection, regardless of HPV Type. Each individual component contributed to improve DNA extraction. The best result was achieved when components a, b and c were combined together.

Example 3. Comparison of DNA Extraction from SurePath LBC Using Diluent 1 at 120° C. and Diluent 2 with Room Temperature Incubation Thirty-six SurePath samples were collected and extracted according to the following two protocols.
1) The No Heat Experiment.

Thirty-six BD Viper™ sample tubes were prepared by adding 0.85 ml of the Diluent 2 described in Example 1. SurePath clinical sample (0.25 ml) was added into each tube. After combining with the samples, the final working buffer concentrations were as follows: 0.255M Tris-HCl, 0.0129M NaCl (with a pH of approximately 7.8) for Diluent 2. The thirty-six tubes were loaded onto the BD Viper™ and 0.8 ml of the sample was used for extraction. DNA was eluted from the sample in 400 µl elution/neutralization buffer. The eluate (20 µl) was mixed with 5 µl of PCR master mix. A real-time PCR assay was used to detect for HPV 16, 18 and 45, and human DNA endogenous control gene HBB.
2) The Heat Experiment.

Thirty-six BD Viper™ sample tubes were prepared to which were added 0.85 ml of the Diluent 1 described in Example 1. SurePath clinical sample (0.25 ml) was added into each tube. After combining the diluent with the samples, the final working buffer concentrations were as follows: 0.77M Tris-HCl, 0.386M NaCl, and 0.77% Triton X-100 (with a pH of approximately 9.0) in Diluent 1. All sample tubes were incubated at 120° C. for 20 min and then cooled for 25 min to room temperature. The thirty-six tubes were loaded onto the BD Viper™ and 0.8 ml of the sample was used for extraction. DNA was eluted from the sample in 400 µl elution/neutralization buffer. The eluate (20 µl) was mixed with 5 µl of PCR master mix. A real-time PCR HPV assays was used to detect for HPV 16, 18 and 45, and human DNA endogenous control gene HBB. HPV 45 and HPV 18 were not detected.

TABLE 3

Comparison of DNA Extraction: i) using Diluent 1 with 120° C. incubation; and ii) Diluent 2 at room temperature incubation.

| | HPV16 | | HBB | | |
|---|---|---|---|---|---|
| | No heat | Heat | No heat | Heat | ΔCt |
| 1 | No Ct | No Ct | 25.28 | 23.97 | 1.31 |
| 2 | No Ct | No Ct | 32.25 | 28.30 | 3.95 |
| 3 | No Ct | No Ct | 31.78 | 27.92 | 3.86 |
| 4 | No Ct | 41.33 | 34.78 | 29.83 | 4.95 |
| 5 | No Ct | No Ct | 34.69 | 29.74 | 4.95 |
| 6 | No Ct | 41.09 | 37.51 | 31.31 | 6.20 |
| 7 | No Ct | No Ct | 32.24 | 26.82 | 5.42 |
| 8 | No Ct | No Ct | 31.93 | 26.88 | 5.05 |
| 9 | No Ct | No Ct | 31.74 | 28.88 | 2.86 |
| 10 | No Ct | No Ct | 28.88 | 25.59 | 3.29 |
| 11 | No Ct | No Ct | 29.41 | 24.93 | 4.48 |
| 12 | No Ct | No Ct | 35.21 | 29.66 | 5.55 |
| 13 | No Ct | No Ct | 28.54 | 25.23 | 3.31 |
| 14 | No Ct | No Ct | 30.66 | 27.54 | 3.12 |
| 15 | No Ct | 35.16 | 32.31 | 26.86 | 5.45 |
| 16 | No Ct | No Ct | 36.29 | 29.39 | 6.90 |
| 17 | 25 | 21.07 | 32.54 | 28.00 | 4.54 |
| 18 | No Ct | No Ct | 35.46 | 29.89 | 5.57 |
| 19 | No Ct | 34.90 | 32.18 | 29.19 | 2.99 |
| 20 | No Ct | No Ct | 28.83 | 24.56 | 4.27 |
| 21 | No Ct | No Ct | 31.64 | 26.72 | 4.92 |
| 22 | No Ct | No Ct | 28.14 | 24.40 | 3.74 |
| 23 | No Ct | No Ct | 26.67 | 25.68 | 0.99 |
| 24 | No Ct | 31.33 | 29.38 | 25.09 | 4.29 |
| 25 | No Ct | No Ct | 32.74 | 31.56 | 1.18 |
| 26 | No Ct | No Ct | 32.91 | 26.57 | 6.34 |
| 27 | No Ct | No Ct | 32.96 | 28.30 | 4.66 |
| 28 | No Ct | No Ct | 35.79 | 29.64 | 6.15 |
| 29 | No Ct | No Ct | 29.96 | 27.84 | 2.12 |
| 30 | No Ct | No Ct | 32.76 | 28.77 | 3.99 |
| 31 | No Ct | No Ct | 31.37 | 24.60 | 6.77 |
| 32 | No Ct | No Ct | 32.79 | 29.07 | 3.72 |
| 33 | No Ct | 42.28 | 30.9 | 27.83 | 3.07 |
| 34 | No Ct | No Ct | 34.58 | 30.51 | 4.07 |
| 35 | No Ct | No Ct | 36.73 | 28.06 | 8.67 |
| 36 | 36.36 | 32.38 | 22.78 | 21.22 | 1.56 |

On average, the heated incubation/Diluent 1 protocol shortened, by 4.29 Ct, the detection of HBB compared to the protocol using Diluent 2 at room temperature incubation. Samples that had the Type 16 HPV DNA (all samples are presumed to have the HBB control DNA whereas not all samples will have HPV of one or more types) exhibited detection with shortened Ct values and therefore became more detectable when using the protocol with heated incubation and Diluent 1 compared with using room temperature incubation and Diluent 2.

Example 4. Comparison of DNA Extraction from SurePath and ThinPrep PreservCyt LBC with or without Heat Stock patient-derived cells were diluted in one of either SurePath or ThinPrep negative clinical specimens at 12500 cells/ml. Thirty-two BD Viper™ sample tubes were prepared to which were added 0.85 ml of Diluent 1. SurePath spiked with patient cells (0.25 ml) was added to 16 sample tubes and ThinPrep spiked with patient cells (0.25 ml) was added to the other 16 sample tubes. After combining the diluent with the samples, the final working buffer concentrations were as stated in Example 1. Eight sample tubes from each group were incubated at room temperature and eight were incubated at 120° C. for 20 minutes. The heated tubes were cooled for 25 minutes to room temperature. The sample tubes were then loaded on the BD Viper™ platform and 0.8 ml of the samples were used for DNA extraction. The DNA was then eluted in 400 µl elution/neutralization buffer. The eluate (20 µl) was mixed with 5 µl of PCR master mix. Twenty copies/reaction of HPV 18 and HPV 45 plasmid DNA targets were post-spiked into each sample for testing the PCR inhibition. The real-time PCR assays were used for detection of HPV 16, 18 and 45, and human DNA endogenous control gene HBB.

TABLE 4

DNA Extraction from SurePath and ThinPrep
PreservCyt LBC with or without heat

| | ThinPrep | | SurePath | |
|---|---|---|---|---|
| Rep | No Heat | Heat | No Heat | Heat |
| HPV16 | | | | |
| 1 | 31.24 | 31.99 | No Ct | 31.64 |
| 2 | 30.89 | 31.37 | No Ct | 31.63 |
| 3 | 30.98 | 31.66 | No Ct | 32.16 |
| 4 | 31.39 | 31.58 | No Ct | 31.71 |
| 5 | 31.02 | 31.15 | No Ct | 31.16 |
| 6 | 31.26 | 31.44 | No Ct | 31.16 |
| 7 | 31.44 | 31.16 | No Ct | 31.48 |
| 8 | 31.85 | 31.33 | No Ct | 31.58 |
| Avg. | 31.26 | 31.46 | | 31.57 |
| HPV45 | | | | |
| 1 | 32.25 | 32.22 | 32.67 | 32.56 |
| 2 | 32.42 | 32.24 | 32.06 | 32.89 |
| 3 | 33.2 | 33.15 | 32.54 | 31.91 |
| 4 | 32.13 | 32.06 | 32.44 | 31.97 |
| 5 | 32.48 | 33.03 | 32.19 | 32.85 |
| 6 | 31.63 | 33.36 | 32.47 | 32.07 |
| 7 | 33.65 | 32.17 | 32.69 | 31.53 |
| 8 | 32.43 | 32.96 | 32.6 | 32.2 |
| Avg. | 32.52 | 32.65 | 32.46 | 32.25 |
| HBB | | | | |
| 1 | 27.73 | 27.52 | 33.33 | 29.02 |
| 2 | 27.99 | 27.09 | 33.63 | 28.88 |
| 3 | 28.08 | 27.17 | 33.43 | 29.25 |
| 4 | 28.21 | 26.89 | 33.28 | 28.71 |
| 5 | 28.12 | 26.98 | 33.38 | 28.37 |
| 6 | 27.98 | 27.04 | 34.3 | 28.36 |
| 7 | 27.99 | 27.02 | 34.07 | 28.29 |
| 8 | 28.43 | 27.38 | 33.96 | 27.84 |
| Avg. | 28.07 | 27.14 | 33.67 | 28.59 |
| HPV18 | | | | |
| 1 | 33.68 | 33.94 | 34.97 | 33.88 |
| 2 | 33.38 | 33.86 | 33.87 | 33.88 |
| 3 | 34.32 | 34.72 | 34.84 | 33.58 |
| 4 | 33.35 | 34.11 | 34.22 | 33.81 |
| 5 | 33.89 | 34.16 | 34.55 | 33.97 |
| 6 | 33.4 | 32.88 | 32.96 | 33.68 |
| 7 | 34.44 | 34.2 | 34.02 | 33.61 |
| 8 | 33.82 | 34.1 | 33.96 | 34.83 |
| Avg. | 33.79 | 34.00 | 34.17 | 33.91 |

Incubating the specimens at 120° C. in Diluent 1 significantly shortened HBB Ct value for both the ThinPrep and SurePath samples. The reduction (compared to the room temperature incubation) was 0.93 Ct for the ThinPrep samples and 5.08 Ct for the SurePath samples. Heat had no statistically significant effect on the detection of HPV16 from ThinPrep, but significantly improved the detection of HPV16 from SurePath.

Example 5. DNA Extraction from SurePath Using Diluent 1 at Varied pH, Temperature and Time The incubation protocol at 114° C. for 10 minutes was used in conjunction with Diluent 1 described in Example 1 (i.e. 1M Tris, 0.5M NaCl and 1% Triton x100). Samples with different pH's (9.0 and 7.8) were used and tested at varied incubation temperatures and times. The different pHs were also evaluated against Diluent 2 of Example 1 (16.67 mM NaCl and 330 mM Tris).

Stock patient-derived cells were diluted in SurePath at a concentration of 12500 cells/ml. Fifty-six sample tubes were prepared for use in BD Viper XTR™ Platform. There were eight samples in each of seven groups. Each of the following buffers (0.85 ml) was added into one of the seven groups group:

a. Diluent 1, pH 9.0 (incubation at 120° C., 20 min)
b. Diluent 1, pH 9.0 (incubation at 120° C., 10 min)
c. Diluent 1, pH 9.0 (incubation at 114° C., 20 min)
d. Diluent 1, pH 9.0 (incubation at 114° C., 10 min)
e. Diluent 1, pH 7.8 (incubation at 120° C., 20 min)
f. Diluent 2, pH 7.8 (incubation at 120° C., 20 min)
g. Diluent 2, pH 9.0 (incubation at 120° C., 20 min)

Aliquots (0.25 ml) of the diluted patient samples were added into each tube of each group. After combining the diluent with the samples, the final working buffer concentrations are as set forth in Example 1. Each group was incubated at its specified temperature and time above. All tubes were then cooled for 25 minutes to room temperature. The tubes were than loaded onto the BD Viper XTR™ and 0.8 ml was used for DNA extraction from the samples. The DNA was eluted in 400 µl elution/neutralization buffer. The eluate (20 µl) of each was mixed with 5 µl of PCR master mix. Twenty copies/reaction of HPV 18 and HPV 45 plasmid DNA targets were post-spiked into each reaction to test for PCR inhibition. The real-time PCR assays were used for detection of HPV 16, 18 and 45, and human DNA endogenous control gene HBB.

TABLE 5

DNA Extraction from SurePath using Diluent 1 with
different pH and at different temperature and time

| | | Diluent 1 | | | | Diluent 1 | Diluent 2 | |
|---|---|---|---|---|---|---|---|---|
| | | 120° C. | | 114° C. | | 120° C. | 120° | |
| | | pH 9, 20' | pH 9, 10' | pH, 9, 20' | pH 9, 10' | pH 7.8, 20' | pH 7.8, 20' | pH 9, 20' |
| HPV16 | | | | | | | | |
| | 1 | 32.36 | 33.57 | 33.4 | No Ct | 30.79 | 33.5 | 35.21 |
| | 2 | 31.29 | 33.24 | 33.11 | No Ct | 30.56 | 32.79 | 33.11 |
| | 3 | 31.18 | 33.23 | 34.02 | 34.84 | 30.55 | 33.05 | 37.78 |
| | 4 | 31.31 | 32.75 | 32.73 | No Ct | 30.96 | 33.48 | 34.43 |
| | 5 | 32.09 | 31.98 | 33.92 | 34.84 | 30.58 | 34.9 | 35.15 |
| | 6 | 31.37 | 32.68 | 32.69 | No Ct | 30.67 | 34.53 | 34.32 |

TABLE 5-continued

DNA Extraction from SurePath using Diluent 1 with different pH and at different temperature and time

| | Diluent 1 | | | | Diluent 1 | Diluent 2 | |
|---|---|---|---|---|---|---|---|
| | 120° C. | | 114° C. | | 120° C. | 120° | |
| | pH 9, 20' | pH 9, 10' | pH, 9, 20' | pH 9, 10' | pH 7.8, 20' | pH 7.8, 20' | pH 9, 20' |
| 7 | 30.74 | 32.31 | 32.4 | No Ct | 30.31 | 34.43 | 35.81 |
| 8 | 31.91 | 33.02 | 32.65 | 36.58 | 30.85 | 33.12 | No Ct |
| Avg. | 31.53 | 32.85 | 33.12 | 35.42 | 30.66 | 33.73 | 35.12 |
| HPV45 | | | | | | | |
| 1 | 33.2 | 34.66 | 34.08 | 34.1 | 33.71 | 34.41 | 33.97 |
| 2 | 33.35 | 34.31 | 33.56 | 33.71 | 34.03 | 34.18 | 34.5 |
| 3 | 34.32 | 33.32 | 33.05 | 34.5 | 34.47 | 33.42 | 34.92 |
| 4 | 34.56 | 32.84 | 33.71 | 34.28 | 32.21 | 33.81 | 34.09 |
| 5 | 33.22 | 34.63 | 34.48 | 33.43 | 34.61 | 33.89 | 33.72 |
| 6 | 34.11 | 34.8 | 34.11 | 33.98 | 33.47 | 34.15 | 33.99 |
| 7 | 34.65 | 31 | 34.45 | 34.53 | 34.12 | 34.47 | 33.59 |
| 8 | 34.8 | 34.38 | 33.98 | 33.47 | 32.24 | 34.23 | 34.09 |
| Avg. | 34.03 | 33.87 | 33.93 | 34.00 | 33.61 | 34.07 | 34.11 |
| HBB | | | | | | | |
| 1 | 32.52 | 36.54 | 33.5 | 37.33 | 31.38 | 33.61 | 36.89 |
| 2 | 32.27 | 34.4 | 34.54 | No Ct | 31.23 | 32.89 | 35.48 |
| 3 | 31.97 | 33.51 | 33.66 | 36.54 | 31.23 | 33.39 | 36 |
| 4 | 32.42 | 32.79 | 33.87 | No Ct | 31.83 | 34.63 | 35.84 |
| 5 | 33.12 | 32.97 | 32.88 | 35.12 | 31.64 | 35.88 | 36.94 |
| 6 | 32.86 | 34.05 | 34.01 | No Ct | 31.42 | 36.71 | 36.63 |
| 7 | 31.79 | 33.53 | 33.41 | 37.14 | 31.33 | 34.26 | No Ct |
| 8 | 32.79 | 34.22 | 34.13 | 31.23 | 31.8 | 34.41 | No Ct |
| Avg. | 32.47 | 34.00 | 33.75 | 35.47 | 31.48 | 34.47 | 36.30 |
| HPV18 | | | | | | | |
| 1 | 32.2 | 34.35 | 35.13 | 34.31 | 33.57 | 33.16 | 34.19 |
| 2 | 33.16 | 33.21 | 32.69 | 33.33 | 33.08 | 34.32 | 33.96 |
| 3 | 34.08 | 33.4 | 33.22 | 33.1 | 33.66 | 33.29 | 34.91 |
| 4 | 31.86 | 33.99 | 33.92 | 33.15 | 34.12 | 33.72 | 34.48 |
| 5 | 33.14 | 33.91 | 33.53 | 33.36 | 33.35 | 32.72 | 33.18 |
| 6 | 33.46 | 34.18 | 33.28 | 33.27 | 33.3 | 33.3 | 34.49 |
| 7 | 33.37 | 33.5 | 33.39 | 33.42 | 33.3 | 34.92 | 33.51 |
| 8 | 33.46 | 34.47 | 35.07 | 32.68 | 33.71 | 34.84 | 33.35 |
| Avg. | 33.09 | 33.88 | 33.78 | 33.33 | 33.51 | 33.78 | 34.01 |

The incubation protocol (114° C., 10 minutes) did not yield the degree of detection for HPV 16 that was obtained when the higher heat protocol was used. However, the same degree of detection was obtained for the spiked HPV 45 and HPV 18, irrespective of the incubation protocol that was used. From this it was concluded that the 114° C. protocol provided a lower degree of DNA extraction than the 120° C. incubation protocol. Similarly, incubation at 120° C. for 10 minutes was not as effective for extracting HPV 16 DNA as incubation at 120° C. for 20 minutes. Extraction and detection of HPV 16 DNA using Diluent 1 at pH 7.8 showed a near 1 Ct improvement compared to extraction and detection using Diluent 1 with a pH 9.0 (for incubation at 120° C. for 20 minutes). Extraction following incubation at 120° C. in Diluent 1 resulted in a significant reduction in assay variability as measured by the standard deviation in detected PCR replicates.

Example 6. Effect of pH on Efficacy of Diluent

Stock patient-derived cells were diluted in SurePath LBC media at 12500 cells/ml. Forty sample tubes were prepared for the BD Viper XTR™ platform. They were separated into five groups. Diluent 1 as described in Example 1 (0.85 ml) with a different pH was added to the tubes in each group. The diluents used were:
 a. Diluent 1, pH 6.6;
 b. Diluent 1, pH 6.7;
 c. Diluent 1, pH 7.3;
 d. Diluent 1, pH 8.0;
 e. Diluent 1, pH 9.0; and
 f. Diluent 1, pH 10.0.

The diluted stock patient cells (0.25 ml) were added to each tube of each group. Each group was incubated at 120° C. for 20 minutes, and then cooled for 25 minutes to room temperature. The samples were then loaded on the BD Viper XTR™ and 0.8 ml of the samples was used for extraction. DNA was eluted from the samples in 400 µl elution/neutralization buffer and the eluate 20 µl was mixed with 5 µl of PCR master mix. Twenty copies of HPV 18 and HPV 45 plasmid DNA targets were post-spiked into each sample to test for PCR inhibition. The real-time PCR assays were used for detecting HPV 16, 18 and 45, and human DNA endogenous control gene HBB.

TABLE 6

Effect of pH on efficacy of Diluent 1

| | pH 6.6 | pH 6.7 | pH 7.3 | pH 8.0 | pH 9.0 | pH 10 |
|---|---|---|---|---|---|---|
| HPV16 Rep | | | | | | |
| 1 | 33.64 | 33.46 | 31.47 | 31.21 | 33.79 | 35.68 |
| 2 | 34.06 | 34.96 | 31.67 | 31.36 | 31.86 | 34.32 |

TABLE 6-continued

Effect of pH on efficacy of Diluent 1

|  | pH 6.6 | pH 6.7 | pH 7.3 | pH 8.0 | pH 9.0 | pH 10 |
|---|---|---|---|---|---|---|
| 3 | 34.58 | 33.10 | 32.33 | 31.70 | 31.99 | 36.30 |
| 4 | 33.66 | 33.15 | 32.40 | 31.49 | 31.61 | 35.73 |
| 5 | 33.46 | 34.90 | 32.32 | 31.85 | 32.00 | 34.36 |
| 6 | 34.41 | 33.14 | 32.12 | 31.61 | 31.96 | 34.51 |
| 7 | 34.66 | 34.93 | 32.25 | 31.58 | 32.12 | 35.15 |
| 8 | 34.15 | 34.18 | 32.27 | 31.57 | 32.36 | 35.83 |
| Avg. HPV45 Rep | 34.08 | 33.98 | 32.10 | 31.55 | 32.21 | 35.24 |
| 1 | 33.78 | 32.88 | 33.38 | 33.28 | 34.09 | 33.35 |
| 2 | 34.56 | 32.95 | 34.40 | 33.41 | 32.83 | 33.56 |
| 3 | 34.08 | 33.69 | 34.69 | 33.41 | 33.41 | 33.84 |
| 4 | 33.15 | 33.45 | 33.65 | 34.41 | 34.11 | 34.64 |
| 5 | 35.39 | 33.27 | 33.59 | 33.74 | 33.45 | 33.70 |
| 6 | 33.21 | 32.51 | 35.39 | 33.77 | 34.14 | 34.38 |
| 7 | 34.19 | 32.77 | 32.93 | 33.59 | 33.49 | 33.21 |
| 8 | 34.6 | 33.92 | 34.24 | 33.58 | 34.29 | 33.89 |
| Avg. HBB Rep | 34.12 | 33.18 | 34.03 | 33.59 | 33.73 | 33.82 |
| 1 | 33.21 | 35.08 | 33.56 | 32.84 | 35.69 | 38.28 |
| 2 | 35.82 | 35.28 | 33.79 | 33.93 | 34.51 | No Ct |
| 3 | 35.37 | 34.87 | 34.25 | 33.41 | 34.29 | 36.61 |
| 4 | 35.38 | 35.00 | 34.23 | 33.61 | 34.47 | 37.64 |
| 5 | 35.64 | 35.12 | 34.21 | 33.96 | 34.45 | 37.68 |
| 6 | 35.50 | 36.04 | 34.15 | 33.70 | 34.80 | 37.98 |
| 7 | 35.58 | 35.16 | 34.70 | 33.34 | 34.53 | 38.37 |
| 8 | 35.80 | 36.08 | 34.42 | 33.56 | 35.01 | 40.15 |
| Avg. HPV18 Rep | 35.66 | 35.33 | 34.16 | 33.54 | 34.72 | 38.10 |
| 1 | 34.18 | 33.19 | 34.10 | 33.69 | 34.70 | 33.59 |
| 2 | 33.87 | 33.36 | 34.28 | 34.07 | 34.78 | 34.36 |
| 3 | 32.54 | 34.17 | 34.01 | 33.42 | 34.05 | 34.17 |
| 4 | 33.42 | 34.36 | 34.77 | 34.02 | 31.75 | 34.96 |
| 5 | 34.5 | 34.64 | 34.37 | 33.96 | 34.51 | 34.08 |
| 6 | 33.58 | 33.89 | 35.73 | 34.28 | 33.82 | 35.70 |
| 7 | 34.22 | 34.27 | 34.16 | 34.31 | 34.49 | 33.20 |
| 8 | 34.63 | 34.83 | 34.11 | 35.42 | 34.33 | 34.55 |
| Avg. | 33.87 | 34.09 | 34.44 | 34.15 | 34.05 | 34.33 |

Figure 1B:
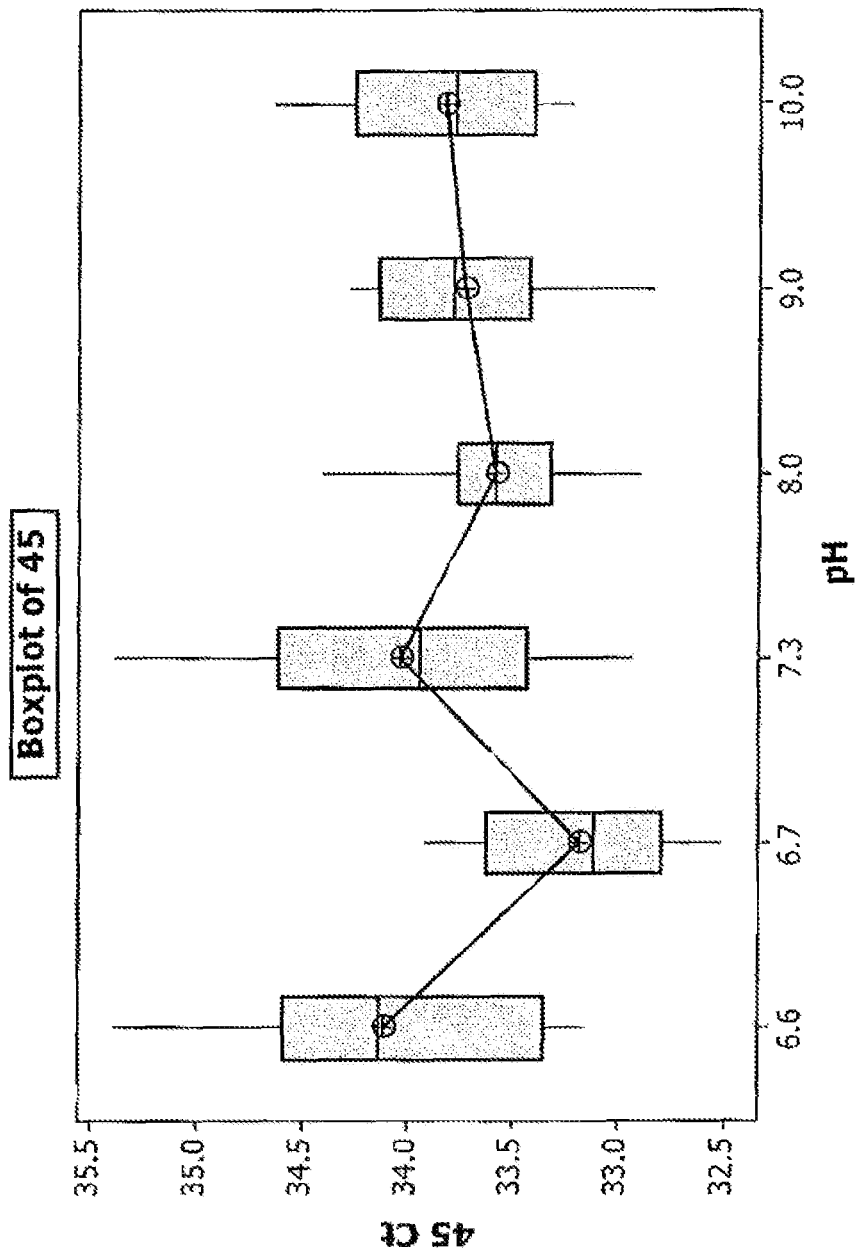
Figure 1C:
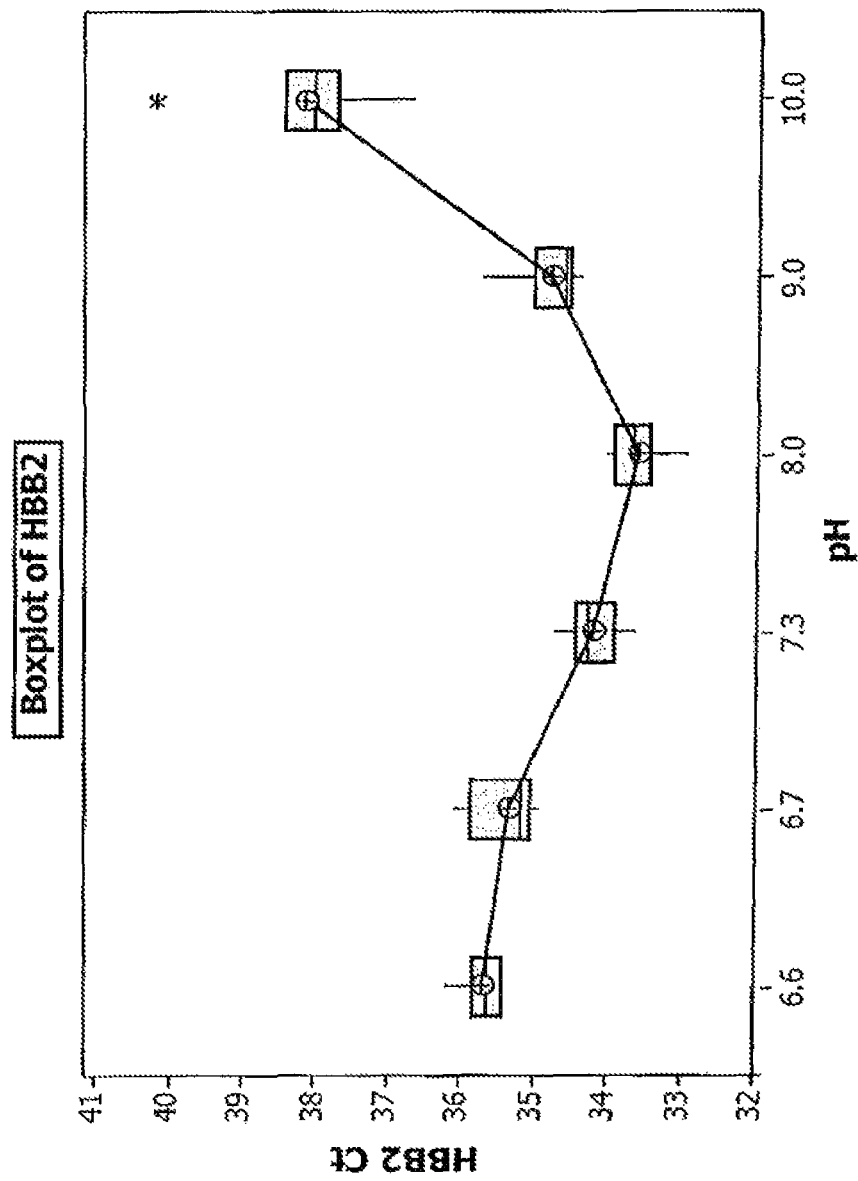

Referring to the results in FIGS. 1A-D, the Diluent 1 with a pH in the range of about 7.3-9 provides the best results in terms of the degree of HPV detection from the sample. This indicates that extraction of DNA from the sample is best when the diluent having a pH in this range is used. Since the detection of spiked HPV 18 and 45 was basically the same at all pH's the improvement in detection of HPV16 and HBB is attributed to better DNA extraction obtained at pH's in range of 7.3 and 9.0.

Example 7. Comparison of DNA Extraction Protocols

Patient-derived cells were harvested and separated into two equal groups. One-half were stored in ThinPrep and the other half SurePath LBC. Both groups had a concentration of $1.14 \times 10^7$ cells/ml. A stock with a cell concentration $2.5 \times 10^4$ cells/ml was prepared from the $1.14 \times 10^7$ cells/ml stock in SurePath media. This stock was used for the following extraction protocols. All extraction protocols were followed by DNA extraction using the BD Viper XTR™ platform.

In the first protocol, eight 226 µl samples of the SurePath stock were spun for 5 minutes at a force of 13,000 g. The resulting supernatant was decanted and resuspended in 1 ml of the Diluent 2 (described in Example 1) that also contained a proteinase K in a concentration of 2 mg/ml. The eight samples were transferred into sample tubes for use with the BD Viper XTR™ platform and incubated at 70° C. for 1 hour. This was followed by extraction on the BD Viper XTR™ platform as described below.

In the second protocol, eight samples (226 µl) of the SurePath stock were diluted (1:4) by adding to the samples 774 µl of Diluent 2 that also contained a proteinase K in a concentration of 2 mg/ml. The eight samples were transferred into sample tubes for use with the BD Viper XTR™ platform and incubated at 70° C. for 1 hour. This was followed by extraction on the BD Viper XTR™ platform as described below.

In the third protocol, eight samples (250 µl) of the SurePath stock were combined with 850 µl of the diluent 2 (described in Example 1). The eight samples were transferred into sample tubes for use with the BD Viper XTR™ platform and incubated at 120° C. for 20 minutes. This was followed by extraction on the BD Viper XTR™ platform as described below.

In the fourth protocol, eight samples (250 µl) of the SurePath stock were combined with 850 µl of Diluent 1 (described in Example 1). The eight samples were transferred into sample tubes for use with the BD Viper XTR™ platform and incubated at 120° C. for 20 minutes. This was followed by extraction on the BD Viper XTR™ platform as described below.

For a negative control, eight 850 µl aliquots of Diluent 2 were combined with 250 µl of clean SurePath media. This was followed by extraction on the BD Viper XTR™ platform as described below All samples were loaded on the BD Viper XTR™ and 0.8 ml of the samples was used for extraction. DNA was eluted from the samples in 400 µl elution/neutralization buffer and the eluate 20 µl was mixed with 5 µl of PCR master mix. The real-time PCR assays were used for detecting HPV 16 and human DNA endogenous control gene HBB.

TABLE 7

Comparison of the heat treatment and Proteinase K (PK) treatment Protocol

| | Protocol | | | | | | | | |
|---|---|---|---|---|---|---|---|---|---|
| | 1 | | 2 | | 3 | | 4 | | 3 |
| | Condition | | | | | | | | |
| | Spin, PK, 70° C. in Diluent 2 | | No Spin, PK, 70° C. in Diluent 2 | | 120° C. in Diluent 2 | | 120° C. in Diluent 1 | | Non-target controls |
| Target | HBB | HPV16 | HBB | HPV16 | HBB | HPV16 | HBB | HPV16 | HBB | HPV16 |
| Rep 1 | 31.38 | 29.49 | No Ct | 32.85 | 32.19 | 29.97 | 29.94 | 28.01 | No Ct | No Ct |

TABLE 7-continued

Comparison of the heat treatment and
Proteinase K (PK) treatment Protocol

| | Protocol | | | | |
|---|---|---|---|---|---|
| | 1 | 2 | 3 | 4 | 3 |
| | | | Condition | | |
| | Spin, PK, 70° C. in Diluent 2 | No Spin, PK, 70° C. in Diluent 2 | 120° C. in Diluent 2 | 120° C. in Diluent 1 | Non-target controls |
| Target | HBB HPV16 | HBB HPV16 | HBB HPV16 | HBB HPV16 | HBB HPV16 |
| Rep 2 | 31.38 29.48 | 32.85 31.21 | 31.30 29.35 | 29.45 27.75 | No Ct No Ct |
| Rep 3 | 31.00 28.92 | 32.26 30.40 | 31.62 29.88 | 29.83 27.96 | No Ct No Ct |
| Rep 4 | 30.55 28.66 | 32.39 30.66 | 31.01 29.02 | 29.72 27.56 | No Ct No Ct |
| Rep 5 | 30.12 28.37 | 32.16 30.06 | 31.88 29.61 | 30.16 28.26 | No Ct No Ct |
| Rep 6 | 30.68 28.86 | 32.15 30.36 | 31.62 29.49 | 29.79 27.83 | No Ct No Ct |
| Rep 7 | 31.09 28.9 | 32.26 30.15 | 31.56 29.51 | 29.95 28.22 | No Ct No Ct |
| Rep 8 | 30.55 28.66 | 32.26 30.23 | 31.61 29.32 | 30.19 28.57 | No Ct No Ct |
| Avg. | 30.84 28.92 | 32.33 30.74 | 31.60 29.52 | 29.88 28.02 | |

Incubation in Diluent 1 at 120° C. yielded the lowest CT values on average for HPV 16. This indicates that, of the protocols tested, the incubation in Diluent 1 provided for the best extraction of DNA from the sample. The protocol that used Diluent 2 with incubation at 120° C. yielded a better result than the result from proteinase K incubation at 70° C. without spin down. Specifically, Diluent 1 reduced the average Ct value of HPV 16 by 0.90, 2.72 and 1.5, respectively, and reduced the average Ct value of HBB by 0.97, 2.45 and 1.72, respectively, when compared with i) proteinase K treatment (following spin down) at 70° C.; ii) proteinase K treatment (No spin down); and iii) incubation at 120° C. in Diluent 2.

Example 8. Extraction from Samples Spiked with Blood

Pooled SurePath and ThinPrep clinical negative specimens were combined with whole blood. The samples had 1%, 2%, 5% and 10% (volume of blood per volume of sample). All samples were incubated at 120° C. in Diluent 1 described in Example 1 for 20 minutes. This was followed by extraction on the BD Viper XTR™ platform using the protocol described in the previous examples. All samples were loaded on the BD Viper XTR™ and 0.8 ml of the samples was used for extraction. DNA was eluted from the samples in 400 µl elution/neutralization buffer and the eluate 20 µl was mixed with 5 µl of PCR master mix. The real-time PCR HPV assay was used for detecting human DNA endogenous control gene HBB.

TABLE 8A

Effect of Blood on Assay (SurePath)

| | Media SurePath | | | | |
|---|---|---|---|---|---|
| Blood (%) | 0 | 1 | 2 | 5 | 10 |
| 1 | 28.62 | 28.66 | 28.97 | 38.66 | No Ct |
| 2 | 30.02 | 28.99 | 29.34 | 29.76 | 28.78 |

TABLE 8A-continued

Effect of Blood on Assay (SurePath)

| | Media SurePath | | | | |
|---|---|---|---|---|---|
| Blood (%) | 0 | 1 | 2 | 5 | 10 |
| 3 | 28.63 | 28.65 | 28.63 | 28.73 | 28.52 |
| 4 | 28.34 | 28.43 | 28.81 | 28.61 | 28.28 |
| 5 | 27.92 | 28.69 | 28.90 | 29.10 | 28.06 |
| 6 | 28.24 | 28.97 | 28.67 | 28.98 | 28.64 |
| 7 | 28.08 | 29.13 | 28.09 | 28.61 | 28.76 |
| 8 | 28.48 | 28.92 | 29.46 | 28.15 | 28.73 |
| Avg. | 28.54 | 28.81 | 28.86 | 28.83 | 28.54 |

TABLE 8B

Effect of Blood on Assay (ThinPrep PreservCyt)

| | Media ThinPrep PreservCyt | | | | |
|---|---|---|---|---|---|
| Blood (%) | 0 | 1 | 2 | 5 | 10 |
| 1 | 31.99 | 30.99 | 31.16 | 30.75 | 30.38 |
| 2 | 32.08 | 31.67 | 30.28 | 30.40 | 29.98 |
| 3 | 31.92 | 31.62 | 31.02 | 30.19 | 30.34 |
| 4 | 31.65 | 31.31 | 31.12 | 30.20 | 30.16 |
| 5 | 31.55 | 31.43 | 30.79 | 30.10 | 30.06 |
| 6 | 31.90 | 31.04 | 30.63 | 30.14 | 30.49 |
| 7 | 31.31 | 31.40 | 30.53 | 30.29 | 29.96 |
| 8 | 31.45 | 31.34 | 30.85 | 29.84 | 29.88 |
| Avg. | 31.73 | 31.35 | 30.80 | 30.24 | 30.16 |

The assay was not affected by high concentration of whole blood, a substance often found in LBC specimens and known inhibitor of PCR reactions. This DNA extraction method delivers suitable DNA for PCR amplification even with high concentration of whole blood present in the clinical samples.

Example 9. DNA Extraction from Formalin-Fixed, Paraffin-Embedded Tissue Slice Formalin-fixed, paraffin-embedded cervical biopsy tissue slices were incubated at 120° C. in 2 ml of Diluent 1 described in Example 1 for 25 minutes. The samples were then cooled to room temperature. After cooling, the samples were subjected to the previously described extraction protocol on the BD Viper XTR™-Platform. All samples were loaded on the BD Viper XTR™ and 0.8 ml of the samples was used for extraction. DNA was eluted from the samples in 400 μl elution/neutralization buffer and the eluate 50 μl was added into PCR master dry mix. The real-time PCR assays were used for detecting HPV subtypes 16, 18, 45, 31, 51, 52, 59, (33,58,56,66), (39,68,35) and human DNA endogenous control gene HBB.

TABLE 9

Viper DNA extraction from Formalin-Fixed, Paraffin-Embedded Tissue slice

| Sample ID | Pre-Cancer/Cancer Pathology Grade | Beta Globin Result | HPV Result |
|---|---|---|---|
| DH0727 | Squamous Cell Carcinoma | Positive | HPV 16 |
| DH0847 | Squamous Cell Carcinoma | Positive | HPV 16 |
| DH0848 | Poorly differentiated Carcinoma | Positive | HPV 18, 52 |
| DH0856 | Squamous Cell Carcinoma | Positive | HPV 18, 31 |
| DH0867 | Cervical Intraepithelial Neoplasia (CIN) III | Positive | HPV 16 |
| DH0869 | Cervical Intraepithelial Neoplasia (CIN) III | Positive | High Risk HPV Negative |
| DH0870 | Cervical Intraepithelial Neoplasia (CIN) III | Negative | HPV Indeterminate |
| DH0873 | Cervical Intraepithelial Neoplasia (CIN) III | Positive | HPV 16 |
| DH0874 | Cervical Intraepithelial Neoplasia (CIN) III | Positive | HPV 16 |
| DH0880 | Cervical Intraepithelial Neoplasia (CIN) III | Positive | HPV 16 |
| DH0892 | Squamous Cell Carcinoma | Positive | HPV 16 |
| DH0896 | Squamous Cell Carcinoma | Positive | HPV (33, 58, 56, 66) |
| DH0898 | Squamous Cell Carcinoma | Positive | HPV 16, 45 |
| DH0900 | Squamous Cell Carcinoma | Positive | HPV 45 |
| DH0902 | Squamous Cell Carcinoma | Positive | HPV 16 |
| DH0903 | Squamous Cell Carcinoma | Positive | HPV 16 |
| DH0904 | Squamous Cell Carcinoma | Positive | HPV 16 |
| DH0905 | Squamous Cell Carcinoma | Positive | HPV 16, 59 |
| DH0910 | Cervical Intraepithelial Neoplasia (CIN) III | Positive | HPV 16 |
| DH0911 | Cervical Intraepithelial Neoplasia (CIN) III | Positive | HPV 16 |
| DH0914 | Cervical Intraepithelial Neoplasia (CIN) III | Positive | HPV 16 |
| DH1408 | Cervical Intraepithelial Neoplasia (CIN) III | Positive | HPV 16, 59 |

In 20 of 22 individual samples, some subtype(s) of HPV DNA were successfully detected. The human endogenous beta-globin gene was detected in 21 of 22 samples. Real-time PCR and HPV subtype specific primers and beta-globin specific primers for HBB were used. The beta globin results indicate that there was no obvious PCR inhibition associated with the current DNA extraction method. The failure to detect beta globin signal in one sample and both beta globin and HPV signal in a second may have been due to lack of sufficient target cells in the section processed for DNA extraction.

Example 10. Extraction of HPV DNA from Patient-Derived Cells Stored in SurePath and ThinPrep LBC Media Using Diluent 1 for Direct Chemical Lysis Stock patient-derived cells were diluted in SurePath and Thinprep LBC at 5000 cells/ml. Sixteen tubes of each sample type had 0.50 ml of the following diluent: 1.5M Tris, 0.386M NaCl and 1.5% Triton X-100 (v/v). The diluent had a pH of 7.9. Diluted patient-derived cells (0.5 ml) in SurePath and ThinPrep were added into each of the sample tubes with diluent. After combining with the samples, the final working buffer concentrations were as follows: 0.75M Tris-HCl, 0.193M NaCl, and 0.75% Triton X-100 (v/v) (with a pH of approximately 7.9). The combined solution was incubated at 120° C. for 20 minutes as direct chemical lysis. Following incubation, the samples were prepared for extraction on the BD Viper™ XTR platform. The extraction protocol previously describe was used. That is, all samples were loaded on the BD Viper XTR™ and 0.8 ml of the samples was used for extraction. Half of the samples were with lysis step during extraction and half of the samples were not. DNA was eluted from the samples in 400 μl elution/neutralization buffer and the eluate 20 μl was mixed with 5 μl of PCR master mix. Twenty copies of HPV 18 and HPV 45 plasmid DNA targets were post-spiked into each sample to test for PCR inhibition. The real-time PCR assays were used for detecting HPV 16, 18 and 45, and human DNA endogenous control gene HBB. The results of the assays are provided below.

TABLE 10

Using pre-warm in diluent as direct chemical lysis followed by DNA Extraction with and without lysis

| Rep | SurePath | | ThinPrep | |
|---|---|---|---|---|
| | No Lysis | Lysis | No Lysis | Lysis |
| HPV16 | | | | |
| 1 | 31.77 | 32.15 | 31.67 | 32.06 |
| 2 | 31.83 | 31.43 | 32.04 | 31.68 |
| 3 | 31.55 | 31.95 | 31.76 | 31.93 |
| 4 | 31.76 | 32.35 | 31.86 | 32.00 |
| 5 | 32.05 | 32.19 | 31.67 | 32.36 |
| 6 | 31.73 | 32.02 | 31.46 | 31.55 |
| 7 | 31.95 | 31.96 | 31.64 | 32.28 |
| 8 | 32.18 | 32.30 | 31.85 | 31.41 |
| Avg. | 31.85 | 32.04 | 31.74 | 31.94 |
| HPV45 | | | | |
| 1.00 | 33.26 | 32.82 | 33.12 | 32.83 |
| 2.00 | 33.10 | 33.03 | 32.92 | 32.61 |
| 3.00 | 32.45 | 31.90 | 32.49 | 33.06 |
| 4.00 | 31.89 | 32.99 | 32.40 | 33.17 |
| 5.00 | 33.47 | 31.92 | 32.63 | 32.13 |
| 6.00 | 33.38 | 32.66 | 32.89 | 31.66 |
| 7.00 | 32.53 | 32.32 | 32.04 | 32.48 |
| 8.00 | 32.98 | 32.95 | 32.23 | 33.47 |
| Avg. | 32.88 | 32.57 | 32.59 | 32.69 |
| HBB | | | | |
| 1 | 31.63 | 32.10 | 31.50 | 32.11 |
| 2 | 30.37 | 31.64 | 31.16 | 31.67 |
| 3 | 31.57 | 31.75 | 31.24 | 31.93 |
| 4 | 31.69 | 31.68 | 31.48 | 31.77 |
| 5 | 31.49 | 31.99 | 31.06 | 31.87 |
| 6 | 32.08 | 31.15 | 31.45 | 31.45 |

TABLE 10-continued

Using pre-warm in diluent as direct chemical lysis
followed by DNA Extraction with and without lysis

| | SurePath | | ThinPrep | |
|---|---|---|---|---|
| Rep | No Lysis | Lysis | No Lysis | Lysis |
| 7 | 31.95 | 31.37 | 31.50 | 31.02 |
| 8 | 32.05 | 32.06 | 31.94 | 31.38 |
| Avg. | 31.60 | 31.72 | 31.42 | 31.65 |
| HPV18 | | | | |
| 1.00 | 33.93 | 34.21 | 34.17 | 33.91 |
| 2.00 | 34.06 | 33.53 | 33.41 | 33.20 |
| 3.00 | 33.00 | 33.05 | 33.71 | 33.47 |
| 4.00 | 33.99 | 33.40 | 33.64 | 33.15 |
| 5.00 | 33.77 | 33.45 | 30.55 | 33.40 |
| 6.00 | 33.69 | 29.50 | 33.40 | 32.60 |
| 7.00 | 33.23 | 32.77 | 33.65 | 33.62 |
| 8.00 | 33.57 | 33.43 | 33.79 | 33.58 |
| Avg. | 33.66 | 32.92 | 33.29 | 33.37 |

The DNA yield for both the extracted DNA (i.e. HPV 16 and HBB) and the spiked DNA (i.e. HPV 45 and HPV 18) is about the same for both the lysis and the no lysis during NA extraction (i.e. direct chemical lysis using one example of the composition and method described herein. This held true for both ThinPrep (TP) and SurePath (SP) media. This indicates that the composition and method described herein serves as a direct chemical lysis of the cells in the sample without need of other enzymatic or chemical lysis steps.

Example 11. Viper DNA Extraction Capability from Patient-Derived Cells Stored in SurePath LBC Media Using Diluent for Direct Chemical Lysis $C_{33}A$ cells that had been stored in SurePath LBC for a month were diluted to $10^8$, $10^7$, $10^6$, $10^5$, $10^4$, $10^3$, 500, 250, 125, 62.5, 31.25 cells/ml. Four (4) replicates were included in each concentration. 0.25 ml of each concentration of SurePath cell stocks (0.25 ml of each concentration) were mixed with 0.75 ml of an HPV diluent (1.0M Tris, 0.257M NaCl, and 1.0% Triton X-100 (v/v); pH of 7.9). Triton X-100 (v/v); pH of 7.9). After the diluent was combined with the samples, the final working concentration of the direct chemical lysis composition was 0.75M Tris-HCl, 0.193M NaCl, and 0.75% Triton X-100 (v/v) (with a pH of approximately 7.9). The samples in diluent were pre-warmed at 120° C. for 20 minutes, and then cooled to room temperature. These samples (0.8 ml) were extracted using the Viper XTR instrument and eluted in 400μ, final volume. DNA eluate (20 μL) was mixed with PCR master-mix (5 μL) in real-time PCR to quantitate the copy number of extracted HBB DNA. Purified human genomic DNA was added to PCR at 100,000, 10,000, 1000, 100, 10, 1 copy/reaction and used for sample DNA quantification. Extraction efficiency was calculated from the ratio of extracted HBB copies quantitated by real-time PCR and total HBB copies based on the input cell number.

TABLE 11

Viper DNA extraction capability utilizing direct
chemical lysis followed by DNA Extraction

| Input Cell Count | Extraction Efficiency |
|---|---|
| $2 \times 10^7$ | 0.440 |
| $2 \times 10^6$ | 0.322 |
| $2 \times 10^5$ | 0.526 |
| $2 \times 10^4$ | 0.809 |
| $2 \times 10^3$ | 0.731 |
| 200 | 0.967 |
| 100 | 0.499 |
| 50 | 0.656 |
| 25 | 0.614 |
| 12.5 | 0.511 |
| 6.25 | 0.345 |
| Avg. | 0.584 |

The extraction capability from the SurePath Media is illustrated in Table 11 using the diluent described above. Table 11 indicates that direct chemical lysis followed by DNA extraction yields greater than 6 logs of linear dynamic range with an average efficiency of 58% using human cervical carcinoma cell line in SurePath media as a model system.

Example 12. Compatibility of Direct Chemical Lysis HPV Diluent with Enzyme Linked Immunosorbent Assay (ELISA) Protein Bio-Marker Detection SiHa cells were resuspended at room temperature in HPV diluent at a working concentration of $6.7 \times 10^6$ cells/ml and were used undiluted and serially two-fold in 1% Bovine Serum Albumin (BSA) in phosphate buffered saline 0.1% Tween. Target antigen was detected in a standard sandwich enzyme linked immunosorbent assay (ELISA). Target antigen was bound to the surface of microwell plates using a primary antibody before being detected using a secondary antibody conjugated with Streptavidin and horseradish peroxidase and a chemiluminescent substrate. FIG. 2 shows results for each of four target analytes (p16INK4a, HPV16 E1E4, MCM2 and MCM6), where the target antigen was readily detected. Antigen integrity was confirmed by Western immunoblotting for two of the target antigens (MCM2 and MCM6) where both the target proteins were found to be full length (approximately 100 Kilodaltons) with no significant degradation products (data not shown). These results demonstrate that HPV diluent buffer is compatible with the recovery and detection of protein bio-markers and could be used for primary nucleic acid detection followed by or preceded with protein bio-marker detection to further improve or refine disease detection.

All references cited herein are incorporated herein by reference in their entirety and for purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method for preparing a sample comprising:
   combining the sample with a direct chemical lysis composition consisting essentially of a) an assay compatible buffer composition consisting of a buffer component and a metal salt component; and b) an assay compatible surfactant selected from the group consisting of polyethylene glycol octylphenyl ether, polysorbate, and a polyethylene glycol based non-ionic surfactant, wherein the sample is a liquid-based cytology sample; and incubating at least a portion of the combination of the liquid-based cytology sample and the direct chemical lysis composition at a temperature that is at least 80° C. for a time sufficient to lyse at least a portion of cells therein.

2. The method of claim 1, wherein the sample comprises a blood sample.

3. The method of claim 1, wherein the sample comprises cells selected from the group consisting of vaginal cells, cervical cells, endocervical cells, anal cells, exfoliated cells, oral cells, throat cells and peritoneal cells.

4. The method of claim 1, wherein the sample is collected by a swab, brush, broom, or biopsy.

5. The method of claim 1, wherein the liquid-based cytology sample comprises at least one constituent selected from the group consisting of formaldehyde, formic acid, methanol, ethanol, buffered formalin, and EDTA.

6. The method of claim 5, wherein the liquid-based cytology sample comprises buffered formalin.

7. The method of claim 1, wherein the direct chemical lysis composition has a pH that is in a range of about 6.6 to about 10.

8. The method of claim 1, where the metal salt is NaCl and a concentration of NaCl in the direct chemical lysis composition is about 0.01 M or greater.

9. The method of claim 8, wherein the buffer component has a concentration in the range of about 0.2 M to about 2M in the direct chemical lysis composition.

10. The method of claim 9, wherein the NaCl concentration is in the range of about 0.01 M to about 1 M in the direct chemical lysis composition.

11. The method of claim 1, wherein the concentration of the non-ionic surfactant is in the range of about 0.01 to about 2 percent (v/v).

12. The method of claim 1, wherein the buffer component is an acid salt of tris(hydroxymethyl)amino methane and the buffer has a concentration that is about 0.75 M in the direct chemical lysis composition, the NaCl has a concentration that is about 0.19 M in the direct chemical lysis composition and the non-ionic surfactant is a polyethylene glycol octylphenyl ether wherein the polyethylene glycol octylphenyl ether has a concentration that is about 0.75 percent (v/v).

13. The method of claim 1, further comprising:
removing at least a portion of the combination of the liquid-based cytology sample and the direct chemical lysis composition wherein the removed portion is also a combination of the liquid-based cytology sample and the direct chemical lysis composition.

14. The method of claim 13, further comprising:
extracting an assay target from the incubated and lysed removed portion of the liquid-based cytology sample; and
assaying the target.

15. The method of claim 1, wherein the incubating temperature is about 100° C. to about 130° C.

16. The method of claim 15, wherein the incubating temperature is about 120° C.

17. The method of claim 15, wherein the time is about ten minutes to about thirty minutes.

18. The method of claim 16, wherein the time is about twenty minutes.

19. The method of claim 14, wherein the assay target is a target nucleic acid and the assay is an amplification assay for the target nucleic acid.

20. The method of claim 19, wherein the target nucleic acid is DNA.

21. The method of claim 19, wherein the target nucleic acid is RNA.

22. The method of claim 19, wherein the amplifying assay is performed by a manual process.

23. The method of claim 14, wherein the extracting is performed by a manual process.

24. The method of claim 14, wherein the extracting and amplifying are performed in an automated process.

25. The method of claim 14, wherein the assay target is a protein and the assay is a detection assay for the protein.

26. The method of claim 25, wherein the protein is a biomarker.

27. The method of claim 26, wherein the biomarker is selected from the group consisting of antibodies and antigens.

28. The method of claim 14, wherein the assay is an Enzyme Linked Immunosorbent Assay (ELISA).

29. The method of claim 14, wherein the sample has at least one constituent selected from the group consisting of: polypeptides, polyaminoacids, and polysaccharides.

* * * * *